US005580562A

United States Patent [19]
Lipsky et al.

[11] Patent Number: 5,580,562
[45] Date of Patent: Dec. 3, 1996

[54] PREPARATIONS AND USES THEREOF FOR IMMUNOSUPPRESSION

[75] Inventors: Peter E. Lipsky; Xue L. Tao; Jian Cai, all of Dallas, Tex.

[73] Assignee: Board of Regents The University of Texas System, Austin, Tex.

[21] Appl. No.: 168,980

[22] Filed: Dec. 17, 1993

Related U.S. Application Data

[63] Continuation-in-part of Ser. No. 862,836, Apr. 3, 1992, Pat. No. 5,294,443, which is a continuation-in-part of Ser. No. 494,113, Mar. 14, 1990, abandoned.

[51] Int. Cl.$^6$ .................. A61K 35/78; C07D 321/00; C07D 307/77
[52] U.S. Cl. .................. 424/195.1; 514/885; 514/908; 549/228; 549/297; 549/298
[58] Field of Search .................. 424/195.1; 514/885, 514/908; 549/228, 297, 298

[56] References Cited

U.S. PATENT DOCUMENTS

| | | | |
|---|---|---|---|
| 4,005,108 | 1/1977 | Kupchan et al. | 260/343.3 R |
| 4,241,536 | 12/1980 | Saint-Firmin | 47/58 |
| 4,328,309 | 5/1982 | Charlmers et al. | 435/126 |
| 5,192,817 | 3/1993 | Takaishi et al. | 549/298 |
| 5,294,443 | 3/1994 | Lipsky et al. | 424/195.1 |

OTHER PUBLICATIONS

Weijiang et al., "Studies on Diterpenoids from *Tripterygium wilfordii*", Acta Academiae Medicinae Shanghai, 13(4):272, 1986, published in China.
Kupchan et al., "Triptolide and Tripdiolide, Novel Antileukemic Diterpenoid Triepoxides from *Tripergium wilfordii*", Journal of the American Chemical Society, 94(20):7194–7195,1972, published in USA.
Zhang et al., "Antineoplastic Action of Triptolide and its Effect on the Immunologic Functions in Mice", Acta Pharmacologica Sinica, 2(2): 128–131, 1981, published in China.
Wenyan et al., "Triptergium in Dermatologic Therapy", International Journal of Dermatology, 24(3):152–157, 1985, published in USA.
Deng et al., "The Structure of Triptodihydroxy Acid Methyl Ester and Wilfortrine", Chemical Abstracts, 107:436, #55718y, 1987, published Columbus, Ohio.
Wu et al., "The Crystal Structure of Triptophenolide Methyl Ester", Chemical Abstracts, 107:712, #96914c, 1987, published in Columbus, Ohio.
He et al., "Structures of Wilforgine, Wilforzine and Wilformine from *Tripterygium wifordii*", Chemical Abstracts, 107:422, π130906p, 1987, published in Columbus, Ohio.
Deng et al., "The Isolation and Structure of Triptonoterpenol", Chemical Abstracts: 107:369, #112684k, 1987, published in Columbus, Ohio.
PCT search report dated 16 Aug. 1991, published in Europe.
Bai et al., "*Tripterygium wilfordii* Hook F in Treatment of Rheumatoid Arthritis and Ankylosing Spondylitis", Biological Abstracts, 87(3), #29969, (189, published in USA.

Zheng et al., "Immunosuppressive Effects of Wilfortrine and Euonine", Chemical Abstracts, 112(3):22, #16029h. 1990, published Columbus, Ohio.
Zhang et al., "Antineoplastic Effect of Triptolide and Its Effect on the Immunologic Functions in Mice", Chemical Abstracts, 95(9):102, #73690w, 1981, published in Columbus, Ohio.
Xia & Chen, "Alkaloids from Stems and Leaves of *Triptergium wilfordii*", Chemical Abstracts, 113(25):38, #224305t, 1990, published in Columbus, Ohio.
*Tripterygium wilfordii* Hook Research Group, "Studies of Total Glycosides of *Trypterygium wilfordii* on Dermatoses", Biological Abstracts, 79(9)762, #80151, 1985, published in USA.
Chang et al., "A Preliminary Study on the Immunosuppressive Activity of Mixed Glycoside of *T. wilfordii*", Biological Abstracts, 79(10), #89135, 1985, published in USA.
Li & Weir, "Radix *T. Wilforii*: A Chines Herbal Medicine with Potent Immunosuppressive Properties", Biological Abstracts, 90(7), #79317, 1990, published in USA.
Wang & Yuan, "A Tablet of *Tripterygium wilfordii* in Treating Lupus Erythmatosus", Chung Hsi I Chieh Ho Tsa Chih (CHINA), 9(7): 388–407, 1989, published in China.
Xu et al., "Tripterygium in Dermatologic Therapy", Int. J. Dermatol., 24(3):152–157, 1985, published in USA.
Su et al., "Comparative Clinical Studdy of Rheumatoid Arthritis Treated by Triptolide and an Ethyl Acetate Extract of *Trypterygium wilfordii*", Chung Hsi I Chieh Ho Tsa Chih (CHINA), 10(3): 131 & 144–146, 1990, published in China.
Tao et al., "A Prospective, Controlled Double-blind, Crossover Study of *Triptergium wilfordii* Hook F in Treatment of Rheumatoid Arthritis", Chin. Med. J. [English] (CHINA), 102(5):327–332, 1989, published in China.
Tao et al., "Effect of an Extract of the Chinese Herbal Remedy *Tripterygium wilfordii* Hook F on Human Immune Responsiveness", Arthritis and Rheumatism, 34(10):1274–1281, 1991, published in USA.
Chen et al., (1987) "Clinical analysis of 10 cases of *Tripterygium wilfordii* Hook caused toxicity", Smposium: Clinical Application of *Tripterygium wilfordii* Hook, Hubei, China, published in China.

(List continued on next page.)

*Primary Examiner*— Douglas W. Robinson
*Assistant Examiner*—Howard C. Lee
*Attorney, Agent, or Firm*—Akin, Gump, Strauss, Hauer & Feld, L.L.P.

[57] ABSTRACT

A *Tripterygium wilfordii* Hook F preparation having an improved $LD_{50}$ in mice, an improved therapeutic activity-:toxic index ratio and a lower amount of triptolide as compared to previous preparations is disclosed. The $LD_{50}$ in mice of the *T. wilfordii* preparation is greater than about 860 mg/kg, the therapeutic activity:toxic index ratio is greater than about $2.6\times10^{-3}$, and the amount of triptolide is less than about 1.3 μg/mg. The preparation is useful for immunosuppression, in particular, the suppression of primary antibody response and suppression of autoimmune disease and for the treatment of rheumatoid arthritis.

17 Claims, 19 Drawing Sheets

OTHER PUBLICATIONS

Zheng et al., (1983) "Studies on toxicity of total glycosides in *Trypterygium wilfordii*", Acta. Acad. Med. Sinicae, 5(2):73, published in China.

Zheng et al., (1983) "Studies on pharmacological actions of total glycosides in *Trypterygium wilfordii* Hook F" Acta Acad. Med. Sinicae, 5:1, published in China.

Cheng et al. (1984) "A preliminary study of the immunosuppressive activity of mixed glycoside of *Tripterygium wilfordii* Hook F", Chinese J. Immunol. 4:331, published in China.

Zheng et al. (1982) "Effect of the decoction of *Tripterygium wilfordii* Hook on immune functions", Fujiang Med. J., 4:222, published in China.

Zuo et al. (1986) "Different effeect of *Tripterygium reglii* on T and cell function" Chinese J. Immunol., 2:232, published in China.

Jia Li(1985) "Chemistry and pharmacology and clinical application of plants of Tripterygim family", Yao Xue Tong Bao, 20:101, published in China.

Tao et el. (1987) "Progressive, controlled, double–blind, cross-over trial of T2 (polyglycosides extracted from *Trypterygium wilfordii* Hook F) in the treatment of rheumatoid arthritis" Chinese J. Int. Med., i 26:399, published in China.

Tao et at. (1988) "Mechanism of treatment of rheumatoid arthritis with *Tripterygim wilfordii* Hook F I. Effect of T2 on secretion of total IgM and IgM-RF by PBMC", Acta. Acad. Med. Sinicae, 10:361, published in China.

Hubei Study Group (1982) "Pharmacological study on the ethanol extract of *Tripterygium wilfordii* Hook F", Zung Cao Yao, 13:27, published in China.

Wei et al. (1988) "Side effects of T2 in the treatment of 106 pateints with glomerular diseases", New Drug and Its Clinical Application, 1(6):37, published in China.

Jiang et al. (1987) "*Tripterygium wilfordii* Hook caused acute toxicity with kidney involvement in 17 cases", Chinese J. Kidney Dis., 3(3): 167, published in China.

Zhang, L S (1986) "Inhibitory effect of celastrol on murine lymphocyte proliferation", Acta. Pharmacol. Sinicae, 7:85, published in China.

Kupchan, S M (1976) "Novel plant derived tumor inhibitor and their mechanisms of action" Cancer Treatment Reports, 60:1115, published in USA.

Zhang et al. (1986) "Studies on Diterpenoids from *Tripterygium wilfordii*" Changhai Yike Da ue Xuebao, 13(4), 267–272, Chemical Abstracts, published in Columbus, Ohio.

Kupchan et al. (1972) "Triptolide and Tripdiolide, Novel Antileukemic Diterpenoid Triepoxides from *Tripterygium wilfordii*" J. Am. Chem. Soc., 94:7194–7195, published in USA.

Kirkman et at. (1991) "Chimeric (human/mouse) CD7 monoclonal antibody treatment in rheumatoid arthritis", Brit. J. Rheumatol., 30 (Suppl. 2):88.

Wassmer et al. (1990) "Therapy of rheumatoid arthritis with CD4 monoclonal antibodies", Arthritis Rheum. 33:2153

Pu & Zhang, "Effects of Triptolide on T Lymphocyte Functions in Mice," *Chemical Abstracts, Pharmacology*, 112:45, #171972d, 1990, published Columbus, Ohio.

Byers et al. (1990) "Patients with rheumatoid arthritis treated with a pan T–lymphocyte immunotoxin: phase II studies" *FASEB J* 4:A1855.

Goldberg et al. (1990) "Preliminary trial of an anti–CD4 monoclonal antibody (MoAb) in rheumatoid arthritis (RA)" *Arthritis Rheum.* 33:S153.

Harris, E. D. (1990) "Rheumatoid Arthritis: Pathophysiology and implications for therapy" *N. Engl. J. Med.* 322:1277.

Horneff et al. (1991) "Treatment of rheumatoid arthritis with an anti–CD4 monoclonal antibody" *Arthritis Rheum.* 34:129.

June et al. (1990) "Increases in tyrosine phosphorylation are detectable before phospholipase C activation after T cell receptor stimulation" *J. Immunol.* 44:1591.

Lipsky, P. E. (1991) "Rheumatoid Arthritis" In Harrison's Principles of Internal Medicine, J. D. Wilson et al. editors, McGraw Hill, Inc. New York, pp. 1437–1443.

Lu, Xiyu et al. The isolation and the structure of triptochlorolide (T4) from *Tripterygium wilfordii*. ACTH Academiae Medicinae Sinica 12(3):157, 1990.

Ma, Pengcheng et al. 16–hydroxytriptolide, a new active diterpene isolated from *Tripterygium wilfordii*. ACTA Pharmaceutica Sinica 26(10):759, 1991.

Minakuchi et al. (1990) "Delineation of the mechanisms of inhibition of human T cell activation by $PGE_2$" *J. Immunol.* 145:2616.

Moreland et al. (1991) "Treatment of refractory rheumatoid arthritis (RA) with a chimeric anti–CD4 monoclonal antibody" *Clin. Res.* 39:309A.

Mustelin et al. (1990) "T cell antigen receptor–mediated phospholipase C requires tyrosine phosphorylation" *Science* 247:1584.

Racadot et al. (1991) "Immunologic follow–up of 13 patien rheumatoid arthritis treated by anti–CD4 monoclonal antibodies" *Br. J. Rheum.* 30(suppl 2):88.

Reiter et al. (1991) "Treatment of rheumatoid arthritis with monoclonal CD4 antibody M–T151" *Arthritis Rheum.* 34:524.

Sewell et al. (1991) "Rapid improvement in refractory rheumatoid arthritis by an interleukin–2 receptor targeted immunotherapy" *Clin. Res.* 39:314A.

Strand et al. (1990) "Treatment of rheumatoid arthritis with an anti–CD5 immunoconjugate: clinical and immunologic findings and preliminary results of treatment" *Arthritis Rheum.* 33:S25.

Tao et al. (1991) "The effect of an extract of Chinese herbal remedy *Tripterygium wilfordii* Hook F on human immune responses" *Arthritis & Rheum.* 34:1274.

Wendling et al. (1991) "Therapeutic use of monoclonal anti–CD4 antibody in RA" *J. Rheumatol.* 18:325.

Zhang X Y et al. (1992) "Prolonged survival of MRL–lpr/lpr mice treated with *Tripterygium wilfordii* Hook F", *Clinical Immun Immunopathol* 62:66–71.

Pei et al. *Zhongguo Yaolixue Tongbao*, vol. 9(1), pp. 68–72, (1993).

Pei et al. *Zhongguo Yaolixue Bao*, vol. 14(3), pp. 238–242, (1993).

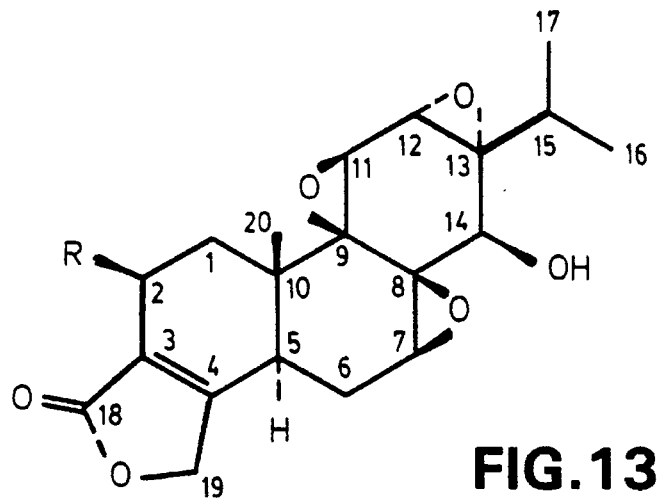
FIG.13
1, R= H
2, R= OH
FIG.14
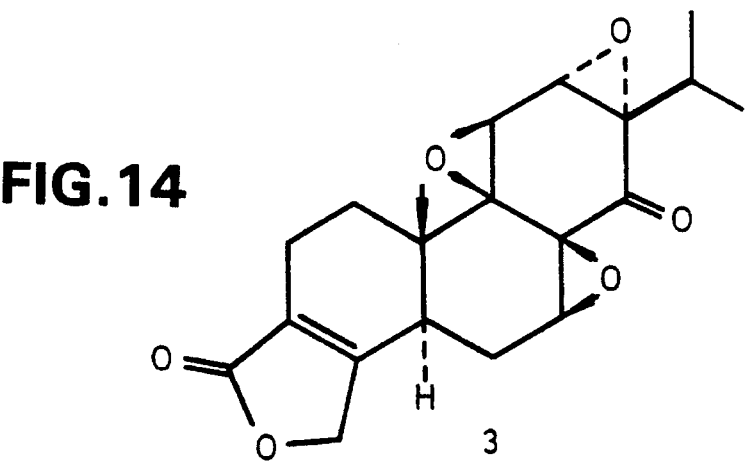
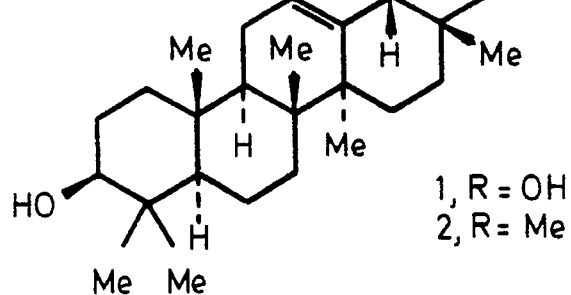
FIG.15
1, R = OH
2, R = Me 1, R = H
2, R = Me

PREPARATIONS AND USES THEREOF FOR IMMUNOSUPPRESSION

The government has rights in the invention developed in parent applications, U.S. Ser. No. 07/862,836 (filed Apr. 3, 1992) and U.S. Ser. No. 07/494,113 (filed Mar. 14, 1990), as research relevant to the development thereof was supported by a grant from the United States government, NIH grant AR-36169.

This application is a continuation-in-part application of Ser. No. 07/862,836 filed Apr. 3, 1992, now U.S. Pat. No. 5,294,443. U.S. Ser. No. 07/862,836 is a continuation-in-part application of Ser. No. 07/494,113, filed Mar. 14, 1990 now abandoned. Application U.S. Ser. No. 07/862,836 is specifically incorporated herein by reference.

BACKGROUND OF THE INVENTION

Rheumatoid arthritis (RA) is a chronic inflammatory disease of uncertain etiology. Since the cause is unknown, treatment has been directed at suppressing the signs and symptoms of chronic inflammation. Although many agents have been documented to decrease pain and swelling temporarily, none has been shown to have a major impact on the course of the disease. While therapeutic modalities have been developed for treatment of this disease[1-4], uniform and persistent suppression of this condition has not been reported. Although current approaches remain promising, alternative means of drug development seem warranted and could yield not only new and effective treatment modalities, but also provide new insights into disease pathogenesis that could serve as the basis of future therapeutic innovations.

An area to search for new therapeutic interventions for different forms of arthritis, and particularly RA and other autoimmune diseases, is that of traditional Chinese medicines. One of these traditional medicines is from *Tripterygium wilfordii* Hook F, a shrub-like vine from the Celastraceae family[5]. *Tripterygium wilfordii* Hook F is known to contain a number of constituents, some of which appear to be toxic[6]. It is known that the leaves, stem, flowers, and the skin of the roots are poisonous and that ingestion can cause death[7-9]. In contrast, the woody portion of the roots of the plant is much less toxic. An extract of *Tripterygium wilfordii* Hook F prepared from the root of the plant, designated $T_2$, has been described in the Chinese literature for the treatment of autoimmune diseases[10-26]. The preparation appeared to contain therapeutic components, and to have a reduced toxicity compared to other available preparations of the plant. The general impression has been that $T_2$ is well-absorbed orally, appears to have at least acceptable toxicity compared with other available preparations of the plant, and as being effective in the treatment of various autoimmune diseases.

The $T_2$ extract has been evaluated in a double-blind placebo controlled cross-over study involving 70 RA patients, these patients having had a mean duration of RA of 6 years[10-11]. Significant improvement in a variety of clinical parameters, particularly ESR, CRP, and Rheumatoid factor titers, was noted after 12 weeks of therapy in the experimental group compared with either baseline measurements or the placebo treated group. Of the patients treated, 82–93% noted improvement in different clinical criteria or laboratory correlates of inflammation. An immunosuppressive activity of $T_2$ may be inferred from the finding that treatment induced inhibition of the production of IgM and IgM rheumatoid factor by the patients' peripheral blood mononuclear cells in vitro[7]. Toxicity, which consisted primarily of skin rash, gastrointestinal complaints and amenorrhea, was reportedly of a generally mild nature, and reversible with cessation of therapy.

The Chinese experience suggested that a daily dosage of 0.8–1.5 mg/kg of $T_2$ was relatively safe and effective. Acute and chronic toxicity studies have been carried out with $T_2$ in China using a variety of animal models. The $LD_{50}$ of $T_2$ in mice was found to be 159.7 ± 14.3 mg/kg[27]. The major chronic toxicity noted in rats administered 30 mg/kg for 90 days was azoospermia and decrease in testicular weight[27]. Lower dosages of $T_2$ did not cause decreases in testicular weight. The toxicity studies, therefore, suggested that $T_2$ exhibited a reasonable safety index and should be able to be administered to patients safely.

Research has begun in China to determine the spectrum of activity of various preparations of *T. wilfordii*. According to the reported results of these studies, extracts of TWH.F were able to inhibit E-rosette formation by guinea pig T cells, mitogen induced IL-2 production by mouse T cells and antigen stimulated migration of rat lymphocytes[28,29]. Components of *T. wilfordii* hook F known as triptonide and triptolide have been reported to inhibit the proliferation of lymph cells induced by concanavalin A[30]. Chloroform/methanol extracts of the plant, referred to as $T_2$ in the literature, have been described as having significant activity in vivo against certain mouse leukemias and in vitro against cells derived from human carcinomas[31]. The capacity of $T_2$ to suppress a number of animal models of autoimmune disease, including adjuvant arthritis and experimental allergic encephalomyelitis, has been reported[28-29,32-36]. Large concentrations of $T_2$ preparations (30 mg/kg) have been reported to suppress delayed type hypersensitivity reactivity in mice and may also suppress graft versus host disease, as well as skin and heart allograft rejection[6,32].

Studies on animal models of autoimmune disease has revealed that various preparations of *T. wilfordii* inhibited manifestations of immune and inflammatory responses in mice, guinea pigs and rats. A water extract of *T. wilfordii* has been examined for its activity in the MRL-lpr/lpr mouse, a model of generalized autoimmune disease which includes glomerulonephritis, vasculitis, arthritis and lymphadenopathy. Dramatic prolongation of survival and reduction of urinary protein were observed in MRL-lpr/lpr mice treated with the water extract at doses of 20 mg/kg three times a week[33,37].

$T_2$-induced toxicity has also been examined in animal models[38-41]. The $LD_{50}$ for acute toxicity in mice was 159.7 ± 14.3 mg/kg. Administration of $T_2$ at 60 mg/kg for 60–80 days, which was higher than that used for the studies of efficacy, did not affect body weight or the histology of most visceral organs except that of the testes and thymus in mice. Long term treatment of dogs with less than 15 mg/kg of $T_2$ for 14.5 months did not affect body weight or hepatic or renal function. No pathological changes of the testes of the treated animals were observed. However, treatment of female mice with $T_2$ at a dosage equal to ~21 mg/kg for 5 months reduced the frequency of pregnancies and the number of fetuses in pregnant mice. $T_2$ treatment also decreased the activity of sperm of rats in a time dependent manner. Treatment of dogs for as long as 14.5 months with 10 mg/kg of $T_2$ caused significant atrophy of the testes.

The $T_2$ examined in the Chinese literature is a crude extract containing a mixture of materials, including various glycosides, alkaloids, and diterpenoids. The active principle, however, has not yet been identified. A few components have been purified, including triptolide, wilfordine, and related compounds, but no particular purified component which accounts for the therapeutic or immunosuppressive activity of $T_2$ exists[40]. High concentrations of triptolide were reported to suppress B and T lymphocyte proliferation and interleukin-2 production by mouse spleen cells[41]. However, the concentrations of the $T_2$ used were sufficiently high that significant nonspecific toxicity undoubtedly occurred.

In China, an ethyl acetate (EA) extract of *T. wilfordii* is manufactured by the Huang Shi Pharmaceutical Company of Hubei Province. This material is extracted from the root with the root skin present, and is known to contain multiple components including terpenes, alkaloids and glycosides. The active ingredient(s) of this preparation, however, is unclear. Some investigators postulate that the diterpene lactone, triptolide and its related compounds account for the therapeutic effect of the EA extract[42–43]. Since triptolide is thought to be one of the most potent compounds and to account for much of the efficacy and toxicity of *T. wilfordii*, the content of tryptolide has been used to standardize the ethyl acetate extract of *T. wilfordii* in China. HPLC analysis carried out by the present inventors demonstrate that the average triptolide content of the Chinese EA extract from different batches manufactured by Huang Shi Pharmaceutical Company, such as those extracts described in Chen et al.[44] and Fang et al[45], was 1.33 μg per mg.

Acute toxicity testing in mice (Hubei white) indicated that the $LD_{50}$ of the EA extract was 608–858 mg/kg. This varied with the source of the plant material used and the season of harvest. Examination of mice dying during the acute toxicity test of the EA extract (714–1400 mg/kg every 3 days, p.o.) showed that the most significant changes developed in lymphatic organs, including induction of atrophy of the thymus. Microscopic examination demonstrated changes that were especially noteworthy in the lymphatic system. These included decreased numbers of nodules and lymphocytes in lymph nodes, spleen and intestine. Mild weight loss and atrophy of the testes along with a decrease in the number and degeneration of spermatocytes were also found in these mice[46].

The ethyl acetate extract produced in China, administered at doses of between 40–80 mg/kg/day, has been reported to inhibit adjuvant induced arthritis and cotton ball induced granuloma in rats[47–49]. This effect was comparable to that of cyclophosphamide or prednisone in the same animal models. At these doses, the EA extract also exerted immunosuppressive effects on both antibody production against sheep red blood cells (SRBC) and delayed skin hypersensitivity induced by dicloronitrobenzene (DNCB) in mice[47].

Various other components have been identified in *T. wilfordii* Hook F including triptolide[49], triptonolide, isoneotriptophenolide and wilforonide[50]. About 0.133% of the Chinese ethyl acetate extract has been identified as triptolide[49]. However, the biological activity of these components has not yet been determined. A need continues to exist for the identification and isolation of the highly therapeutically active components in *T. wilfordii* without the disadvantages associated with currently available preparations of the plant, such as in the $T_2$ preparation. Further characterization of the potentially therapeutically useful components in the plant would provide clinically valuable treatment alternatives for autoimmune diseases, including rheumatoid arthritis, systemic lupus, erythematosus and psoriasis, as well as other forms of immunosuppression.

Thus, an object of the present invention is to provide less toxic yet biologically potent preparations of *T. wilfordii* Hook F, and isolated components thereof, than those currently available. Accomplishment of this object will provide a *T. wilfordii*-derived product that is more clinically acceptable with a reduced toxicity risk for use in humans. An additional object of the invention is to provide improved methods for treating immunosuppression, such as in the treatment of autoimmune disease, and particularly rheumatoid arthritis.

SUMMARY OF THE INVENTION

The above described objects and many others are accomplished with the preparations described in the present disclosure. The invention provides a unique, improved preparation of *T. wilfordii* root that demonstrates a more desirable therapeutic activity:toxic index ratio as compared to other preparations previously described in the literature. The woody portion of the root is used in the preparations found to have these particular advantages. The woody portion of the root is defined for purposes of describing the present invention as that portion of the root that has the skin removed. The decreased toxicity of the claimed preparations may in part be provided by the removal of the plant root skin.

The significant findings presented in the present disclosure include the observation that the preparations of the invention evidence essentially no loss in biological therapeutic activity, yet have significantly reduced toxicity. This was a most unexpected and surprising finding, as prior to the work of the present inventors, it was unknown whether the biological activity of the root preparations would be retained if the components responsible for the toxicity of the plant were removed, or whether the component responsible, at least in part, for the therapeutic potential of the plant was also responsible for toxicity.

The reduced toxicity of the preparations of the *Tripterygium wilfordii* Hook F root provided by the present invention is demonstrated by its $LD_{50}$ in mice, which is greater than about 860 mg/kg. Expressed as a range, the $LD_{50}$ of the preparation is between about 860 mg/kg to 1300 mg/kg. As demonstrated by the inventors, the EA extract produced in Texas is demonstrated to have an $LD_{50}$, more preferably, about 1250 mg/kg. The $LD_{50}$ of the preparation is much higher than that observed with other TWF preparations, as shown herein, and therefore, are considerably less toxic (i.e., requiring higher does to kill).

The *T. wilfordii* preparation is further defined as having a significantly improved therapeutic activity:toxic index ratio over preparations known in the art, this ratio being greater than about $2.6 \times 10^{-3}$, or preferably, from about $2.6 \times 10^{-3}$ to $4.5 \times 10^{-3}$ or more preferably, about $4.5 \times 10^{-3}$. The therapeutic activity:toxic index ratio is calculated from an $ID_{50}$ in vitro T-cell proliferation/$LD_{50}$ ratio.

The present inventors have observed that $T_2$ exerts a number of immunosuppressive effects on human immune responses. $T_2$ has also been observed by the present inventors to cause a concentration dependent inhibition of PHA induced $^3$H-thymidine incorporation by human T lymphocytes, with an $ID_{50}$ of approximately 0.2 μg per ml. Mitogen induced IL-2 production by purified T cells is also inhibited by a similar concentration of $T_2$.

The present *Tripterygium wilfordii* Hook F preparation is also described as having less than about 1.3 μg/mg triptolide or preferably, about 0.2–1.3 μg/mg triptolide, or more preferably, about 0.2 μg/mg triptolide. While the preparation may be obtained by any means of chemical extraction techniques that yield a product having the described therapeutic activity:toxic index ratio and triptolide concentration, those techniques most preferred are ethyl acetate extraction of the root or by an ethanol extraction followed by an ethyl acetate extraction of the root.

A further embodiment of the present invention is a *Tripterygium wilfordii* Hook F preparation having less than about 1.3 µg/mg triptolide obtained by a process comprising the steps of i) obtaining woody portions of roots of a *Tripterygium wilfordii* Hook F plant and removing the skins; and ii) extracting the woody portions with a solvent to produce a *Tripterygium wilfordii* Hook F preparation. The preparation has less than about 1.3 µg/mg triptolide and the solvent is most preferable being ethyl acetate. The extracting step may further include extracting with a first solvent and then with a second solvent, the first solvent most preferably being ethanol and the second solvent most preferably being ethyl acetate.

A most preferred embodiment of the present invention is a *Tripterygium wilfordii* Hook F preparation having a therapeutic activity:toxic index ratio greater than about $2.6 \times 10^{-3}$, the preparation obtained by a process comprising the steps of i) obtaining woody portions of roots of a *Tripterygium wilfordii* Hook F plant and removing the skin; ii) extracting the woody portions with ethanol to produce an ethanol extract; and iii) extracting the ethanol extract with ethyl acetate to form a *Tripterygium wilfordii* Hook F preparation. The preparation has a therapeutic activity:toxic index ratio greater than about $2.6 \times 10^{-3}$ and an $LD_{50}$ in mice of greater than about 860 mg/kg, and less than about 1.3 µg/mg triptolide. A most preferred embodiment of the present invention includes the steps of drying the woody portions of the skinned roots to form a dried woody portion; grinding the dried woody portion to form a powder; and extracting the powder with ethanol to produce an ethanol extract; following the obtaining step aforedescribed. Most preferably, the woody portions of the root are to be dried under open sunlight.

Turning to still another aspect of the claimed invention, a method for immunosuppression is provided. In one embodiment, the method comprises administering a preparation of *Tripterygium wilfordii* Hook F having an $LD_{50}$ in mice of greater than about 860 mg/kg in a therapeutically effective amount to a patient in need of such treatment. The immunosuppression may be suppression of antigen or mitogen induced T-cell proliferation, immunoglobulin synthesis or production of interleukin-2 and the suppression of immunoglobulin synthesis may be suppression of primary antibody response. The immunosuppression may be the suppression of autoimmune disease where the autoimmune disease is rheumatoid arthritis, systemic lupus erythematosus or psoriasis. The therapeutically effective amount is about 30–240 mg/day and has less than about 1.3 µg/mg triptolide. A most preferred embodiment of the present invention is a method for suppressing rheumatoid arthritis in a patient. In a particularly preferred embodiment, the method comprises administering about 30–240 mg/day of a *Tripterygium wilfordii* Hook F root extract preparation having an $LD_{50}$ in mice of greater than about 860 mg/kg to the patient to suppress rheumatoid arthritis wherein the preparation contains less than about 1.3 µg/mg triptolide. This preparation of TWH.F is described in the present invention as the ethyl acetate or TEA (Texas ethyl acetate) extract.

The present invention also discloses an isolated wilforonide component of a 924 fraction obtained from the EA extraction of *T. wilfordii* Hook F root. Both the 924 fraction and the isolated wilforonide are demonstrated to have significant biological activity, measured in terms of PHA-induced T cell proliferation and PHA-induced IL-2 production, and an inhibitory effect on antigen-induce T cell proliferation. The advantages attributable to these preparations are a significant decrease in relative toxicity as compared to other *T. wilfordii* preparations. The invention encompasses methods for immunosuppression comprising administering the wilforonide in a therapeutically effective amount to an animal in need of treatment for immunosuppression. By way of example, such immunosuppression may constitute suppression of antigen or mitogen-induced T-cell proliferation, immunoglobulin synthesis or production of interleukin-2. The immunosuppression may also be defined as suppression of immunoglobulin synthesis such as suppression of immunoglobulin synthesis or suppression of primary antibody response.

Methods for treating autoimmune disease with wilforonide preparations are also provided. These methods comprise administering the wilforonide in a therapeutically effective amount to an animal in need thereof. By way of example, such autoimmune diseases may include rheumatoid arthritis, systemic lupus erythematosus or psoriasis. In a most preferred embodiment, the method is expected to provide an effective treatment for the autoimmune disease of rheumatoid arthritis. While particular doses of wilforonide that are therapeutically effective may be determined using standard pharmacological profiles of the drug in clinical trials, it is expected that a therapeutically effective amount of wilforonide for the treatment of autoimmune disease or for immunosuppression generally will be between about 3 mg/day to about 25 mg/day.

The wilforonide of the invention have significantly reduced toxicity, which may be attributable to their relatively low concentration of triptolide. It is anticipated that the wilforonide preparations include no detectable triptolide (not detectable by HPLC).

In still another aspect of the invention, a method for treating rheumatoid arthritis through the administration of wilforonide to an animal in need thereof is provided. Again, wilforonide has been demonstrated by the present inventors to have relatively low toxicity, and therefore is expected to provide the aforedescribed therapeutic activity without cell cytoxic effects.

The following abbreviations are used throughout the description of the present invention.

| | |
|---|---|
| CRP | = C reactive protein |
| DAG | = diacylglycerol |
| ESR | = erythrocyte sedimentation rate |
| FACS | = fluorescence-activated cell sorter |
| Ig | = immunoglobulin |
| IL-2 | = interleukin-2 |
| IL-2R | = interleukin-2 receptor |
| IP | = phosphatidyl inositol triphosphate |
| MAb | = monoclonal antibodies |
| NHS | = normal human serum |
| PBMC | = peripheral blood mononuclear cells |
| PDB | = phorbol dibutyrate |
| PHA | = phytohemagglutinin |
| PKC | = protein kinase C |
| RA | = rheumatoid arthritis |
| SA | = formalinized *Staphylococcus aureus* |
| SK | = streptokinase |
| SRBC | = sheep red blood cells |
| $T_2$ | = a chloroform/methanol extract from the woody portion of *Tripterygium wilfordii* Hook F |
| TT | = tetanus toxoid |

BRIEF DESCRIPTION OF THE DRAWINGS

In FIG. 6A, B cells ($5\times10^4$/well) were stimulated with SA (o) or SA+IL-2 (o), and in FIG. 6B with SA+IL-2 in the presence of varying concentrations of $T_2$. [$^3$H]-TdR was determined after a 5-day incubation (FIG. 6A). Supernatants were harvested after a seven-day culture and assayed for IgM (■), IgG (o) and IgA (o) content (FIG. 6B). Results are the mean ± SEM of 3 experiments.

FIG. 13 schematically shows the structure of triptolide (1) and triptodiolide (2).

FIG. 14 schematically shows the structure of triptonide.

FIG. 15 schematically describes the structure of wilfortrine (1) and wilfortrine methyl ester (2).

DESCRIPTION OF PREFERRED EMBODIMENTS

The present invention concerns the use of *Tripterygium wilfordii* Hook F extracts to suppress immune function, particularly for the treatment of autoimmune diseases. The *T. wilfordii* preparation may be obtained according to a variety of extraction protocols, including ethanol extraction of *Tripterygium wilfordii* Hook F roots, the skin of the roots having been removed prior to processing the root. As an additional example, the preparation is prepared by ethyl acetate extraction (Example 5).

Example 1 concerns studies on the effect of the *Tripterygium wilfordii* Hook F preparation on human lymphocyte function. Interleukin-2 production by T cells is inhibited by the TWH.F extract by inhibiting gene transcription, while the expression of IL-2 receptors is not affected. The *Tripterygium wilfordii* Hook F preparation is also shown to suppress proliferation of B cells and immunoglobulin production by B cells. The studies described in Example 2 indicate that signaling pathways are not affected by the *Tripterygium wilfordii* Hook F preparation, demonstrating the selective nature of the agent's inhibitory activity. Example 3 concerns studies on the effect of the *T. wilfordii* preparation in the treatment of patients with rheumatoid arthritis. Example 4 describes the components of the $T_2$ *T. wilfordii* Hook F preparation and toxicity thereof. Example 5 describes the *T. wilfordii* Hook F preparation obtained by ethyl acetate extraction in Texas (TEA), while Example 6 demonstrates the in cellulo (intact cell effects) activity of the TEA extract. Example 7 provides in vivo studies with the *T. wilfordii* ethyl acetate extract. Example 8 provides a comparative toxicity study of various *T. wilfordii* preparations. Example 9 describes a technique that may be used for determining the dose schedule of TEA for use in vivo. Example 10 describes the characterization and identification of a fraction '924' from the TEA extract and Example 11 describes immunosuppressive effects of wilforonide.

EXAMPLE 1

Effect of $T_2$ on Human Lymphocyte Function

This example describes the effect of the *T. wilfordii* preparation, $T_2$, on in vitro immune responsiveness of human peripheral blood mononuclear cells (PBMC) obtained from normal individuals. It was found that the preparation exerted a concentration-dependent profile of suppressive activity on both T cell and B cell functions, whereas the functional activities of monocytes were more resistant to the suppressive effects of this *T. wilfordii* preparation with chloroform/methanol.

Methods

Cell Preparation.

PBMC were obtained from the blood of healthy adults by centrifugation on sodium diatrizoate/Ficoll gradients (Sigma, St. Louis, Mo.). Monocytes were isolated from PBMC by centrifugation on Sepra-cell-MN (Sepratech, Oklahoma City, Okla.) or by glass adherence. The monocytes obtained from the two procedures were used to examine interleukin-1 (IL-1) production and antigen presentation, respectively. For purification of T cells and B cells, PBMC were incubated with L-leucine methyl ester HCl (Sigma) for 45 minutes at room temperature to deplete monocytes and natural killer cells[51]. The resultant lymphocytes were rosetted with neuraminidase-treated sheep red blood cells (SRBC) and were then separated by Ficoll/diatrizoate centrifugation[52]. T cells were further purified by passage of the rosette-positive population over a nylon-wool column to remove residual B cells and monocytes[53]. B cells were prepared from the initial population of rosette-negative cells by removing any remaining cells that formed rosettes with neuraminidase-treated SRBC.

Staining with monoclonal antibodies (MAb) to CD3 and CD20 and analysis with the fluorescence-activated cell sorter (FACS) indicated that the T cell and B cell populations were more than 96% and 90% pure, respectively. T cells were incubated with mitomycin c (0.1 mg/ml) for 45 minutes and then washed thoroughly[54].

Reagents,

The *T. wilfordii* preparation, $T_2$, used in these studies was a chloroform/methanol extract prepared from the woody portion of the roots of TWH obtained from Taizhou Pharmaceutical Company (Taizhou, Jiang Su, People's Republic of China). This preparation, $T_2$, contained more than 8 different compounds including glycosides, diterpenoids, alkaloids, and ketones. Before use, the extract was dissolved in DMSO and further diluted with culture medium. Phytohemagglutinin (PHA; Wellcome Reagents, Research Triangle Park, N.C.), phorbol dibutyrate (PDB; Sigma), ionomycin (Calbiochem, San Diego, Calif.), and the anti-CD3 MAb, 64.1, were used for T cell activation[55]. MAb 64.1 was purified as previously described [Hansen et al., "T cell protocol", *Leukocyte Typing*. Edited by Bernard, et al. Berlin, Springer-Verlag, 1982]. Human recombinant interleukin-2 (rIL-2; Cetus, Emeryville, Calif.) and/or formalinized *Staphylococcus aureus* (SA; Calbiochem) was used for B cell activation. The MAb against the α chain of the IL-2 receptor (IL-2R), anti-Tac, was obtained from Dr. Thomas Waldmann (NIH, Bethesda, Md.) and was used to analyze IL-2R expression. Interleukin-1 (Cistron Technology, Pine Brook, N.J.) was purchased for standardization of the IL-1 assay. Affinity-purified goat anti-human IgA, IgG, and IgM and similar antibodies conjugated to horseradish peroxidase were purchased from Tago (Burlingame, Calif.). Streptokinase (SK) and tetanus toxoid (TT) were purchased from Hoechst-Roussel (Somerville, N.J.) and MCDC Biologics (Jamaica Plain, Mass.), respectively.

Cell Culture and Assay of Lymphocyte DNA Synthesis.

T cells ($1\times10^5$/well) or B cells ($5\times10^4$/well) alone or B cells with mitomycin c-treated T cells ($1\times10^5$/well) were cultured in RPMI 1640 medium (Hazleton Biologics, Lenexa, Kans.) supplemented with 10% fetal calf serum, penicillin G (200 units/ml), gentamicin (10 μg/ml), and L-glutamine (0.3 mg/ml) in 96-well microtiter plates in a total volume of 200 μl, with or without the stimuli indicated, and in the presence or absence of various concentrations of $T_2$. The final concentration of DMSO in culture was 0.02–0.002%. This concentration of DMSO had no effect on any of the responses analyzed.

For both T and B cell activation, immobilized anti-CD3 (MAb 64.1) stimulation was used. This MAb was immobilized by incubating 50 μl (5 μg/ml) in each well for at least 2 hours at room temperature. The excess soluble antibody was removed before cell culture (Hansen, supra). Cells were cultured for the indicated duration, and then pulsed with 1 μCi of $^3$H-thymidine, ($^3$H-TdR; New England Nuclear, Boston, Mass.) for the last 12 and 18 hours for T cell and B cell cultures, respectively. $^3$H-TdR uptake was measured in a liquid scintillation counter. All data are expressed as the mean counts per minute of 3 replicate determinations[56].

IL-1 Production Assay.

Monocytes ($1\times10^5$/well) were suspended in RPMI 1640 medium with 1% normal human serum (NHS) and cultured with or without lipopolysaccharide (10 μg/ml) in the presence or absence of various concentrations of $T_2$ for 24 hours. The culture supernatants were collected, and serial dilutions were assayed for IL-1 using C3H/HeJ murine thymocytes as described elsewhere[57]. Concentrations of $T_2$ contained in the dilutions of supernatants had no effect on DNA synthesis by C3H/HeJ thymocytes.

IL-2 Production Assay.

T cells ($1\times10^5$/well) were incubated with or without PHA (1 μg/ml) or immobilized anti-CD3 in the presence or absence of various concentrations of $T_2$ for 24 hours. Cell-free supernatants were harvested, serial dilutions were made, and IL-2 content was assayed with CTLL-2 cells as described previously[58].

IL-2R Expression.

T cells were cultured with or without the indicated stimuli in the presence or absence of various concentrations of $T_2$ for 36 hours. After washing, the cells were stained with saturating concentrations of anti-Tac or a mouse IgG control MAb, followed by fluorescein isothiocyanate-conjugated goat anti-mouse Ig antibody (Cappel, West Chester, Pa.). The samples were fixed with 1% paraformaldehyde and analyzed with a FACSTAR (Becton Dickinson, Mountain View, Calif.) flow cytometer, using a single-histogram statistics program (Davis, supra).

Measurement of Ig Synthesis.

The amount of IgG, IgA, and IgM in the culture supernatants of B cells stimulated with SA plus rIL-2 in the presence or absence of $T_2$ for 7 days was determined using an isotype-specific enzyme-linked immunosorbent assay method. Quantitation of the Ig in the supernatants was then determined by comparison with a standard curve. The sensitivity of the assay is 15 ng/ml for IgA and IgG, and 30 ng/ml for IgM[59].

Results

Effect of $T_2$ on Human T Cell Responsiveness.

Figure 1:
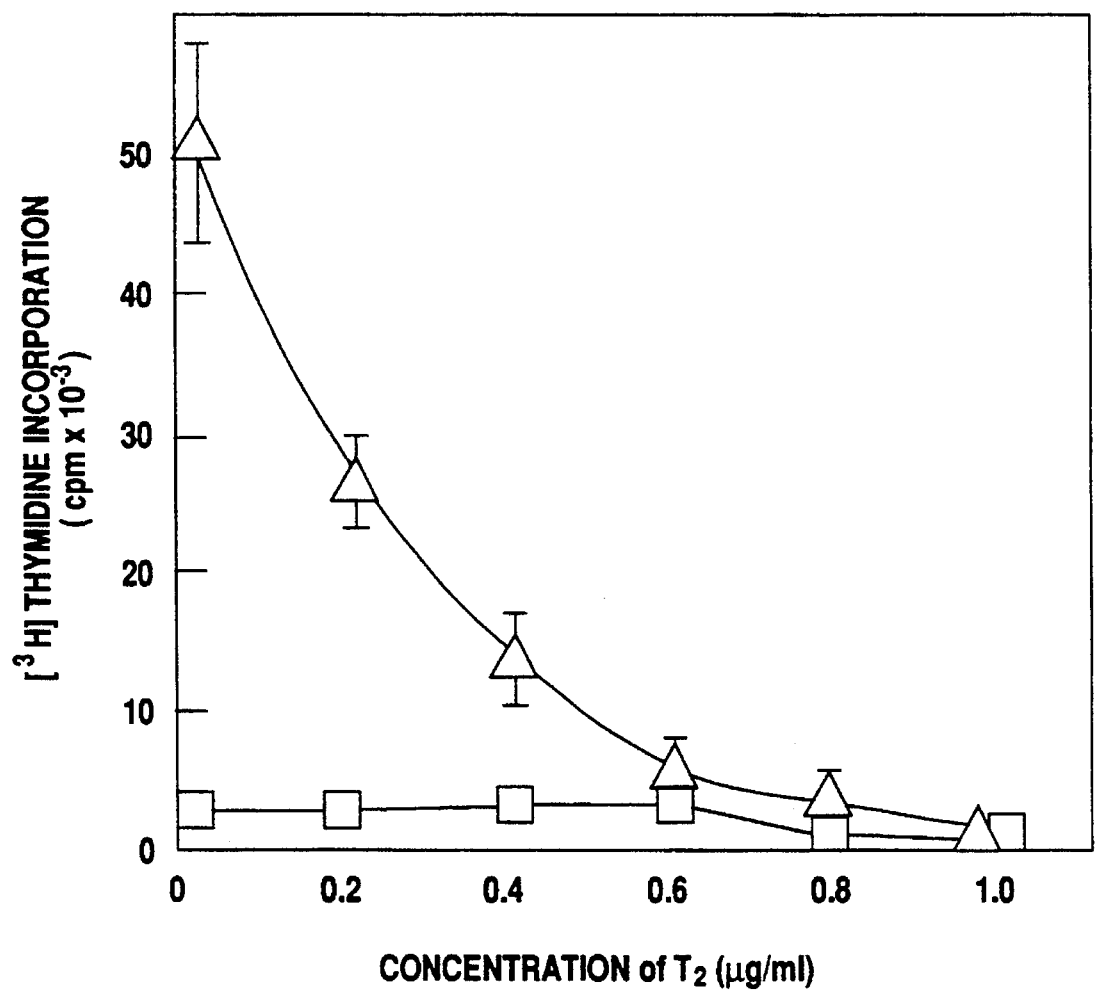
FIG. 1. Effect of $T_2$ on T cell proliferation. T cells ($1 \times 10^5$/well) were cultured with medium (□) or PHA (△) in the presence or absence of varying concentrations of $T_2$ as indicated for 3 days. Results represent the mean cpm ± SEM of three experiments.
Figure 2A:
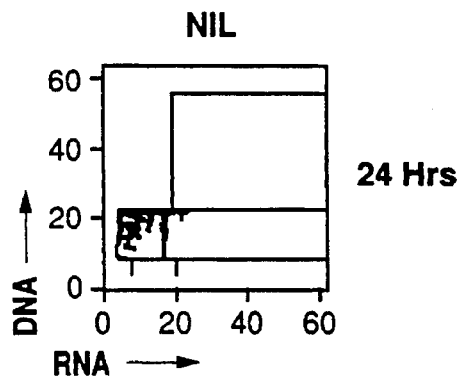
FIGS. 2A–2L. Effect of $T_2$ on cell cycle progression of human T cells. T cells ($1\times10^5$/well) were cultured with or without PHA (1 ug/ml) in the absence or presence of the indicated concentrations of $T_2$ for 24, 48 or 72 hrs. The samples were harvested, stained with acridine orange, and analyzed with an ORTHO flow cytometer using the CICERO program to determine the position of cells in the cell cycle as assessed by their RNA and DNA content.
Figure 2D:
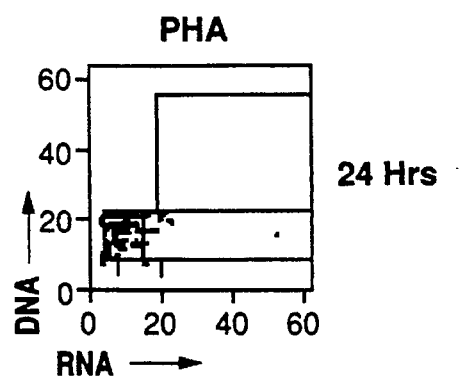
Figure 2B:
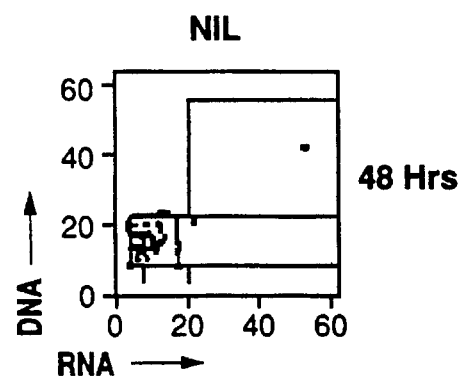
Figure 2E:
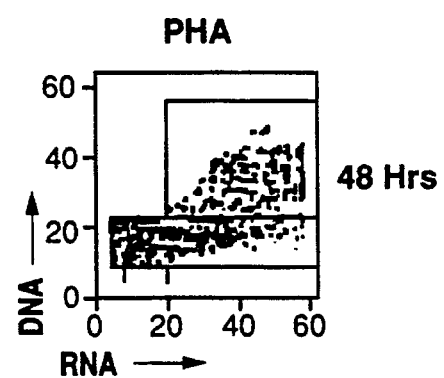
Figure 2C:
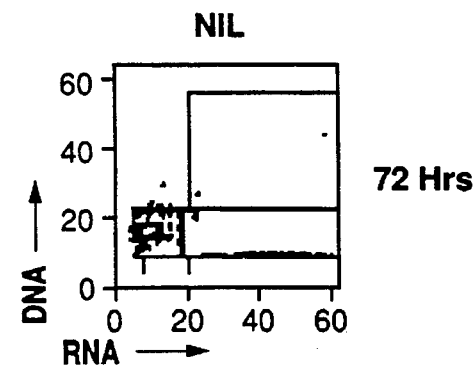
Figure 2F:
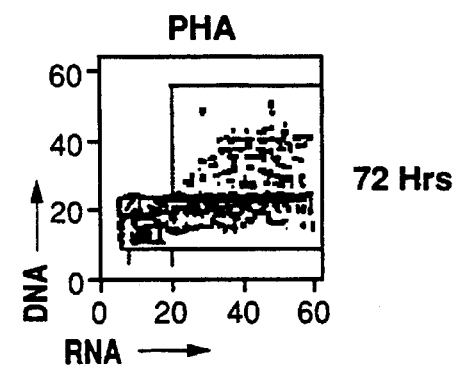
Figure 2G:
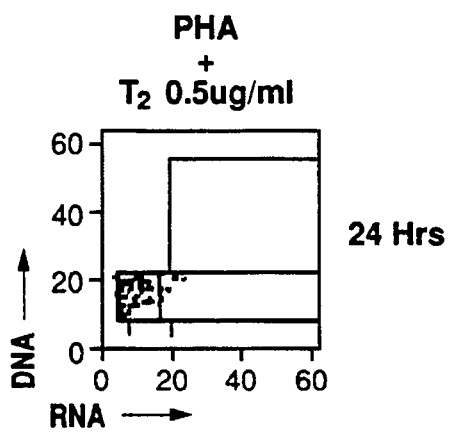
Figure 2J:
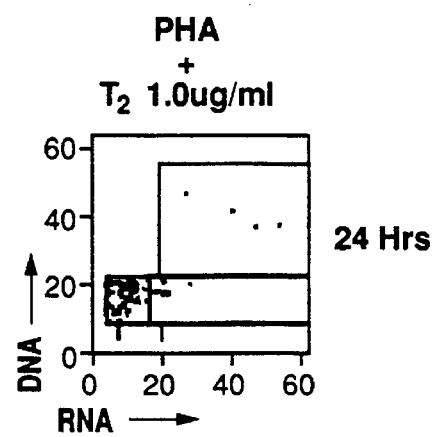
Figure 2H:
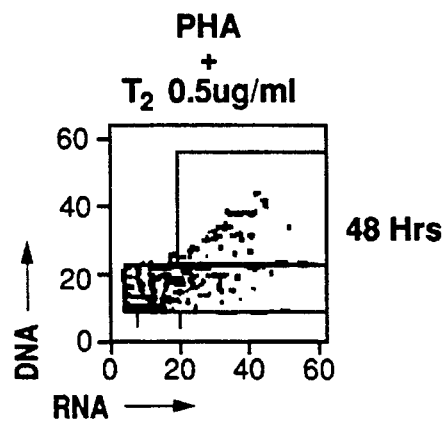
Figure 2K:
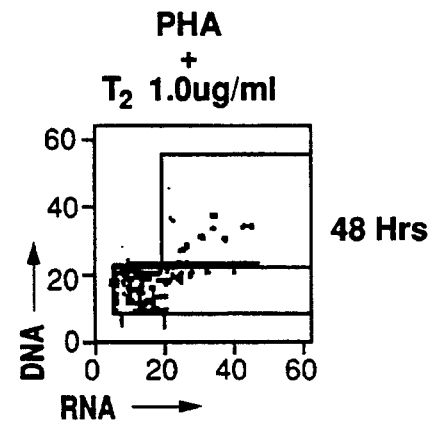
Figure 2I:
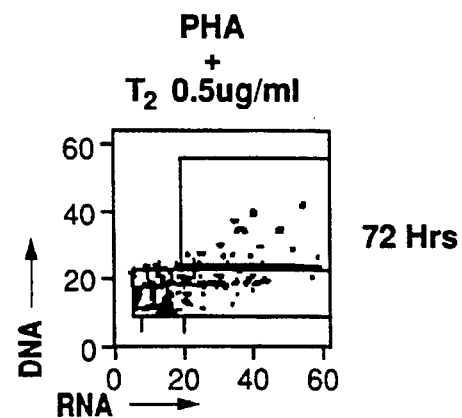
Figure 2L:
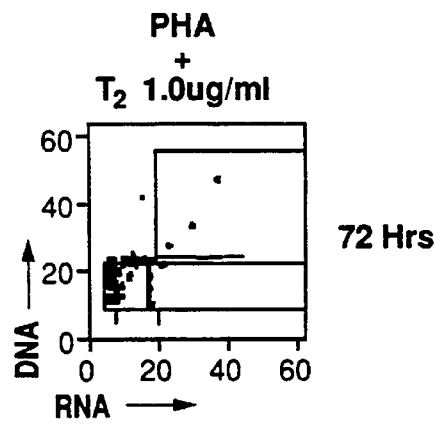
Figure 3:
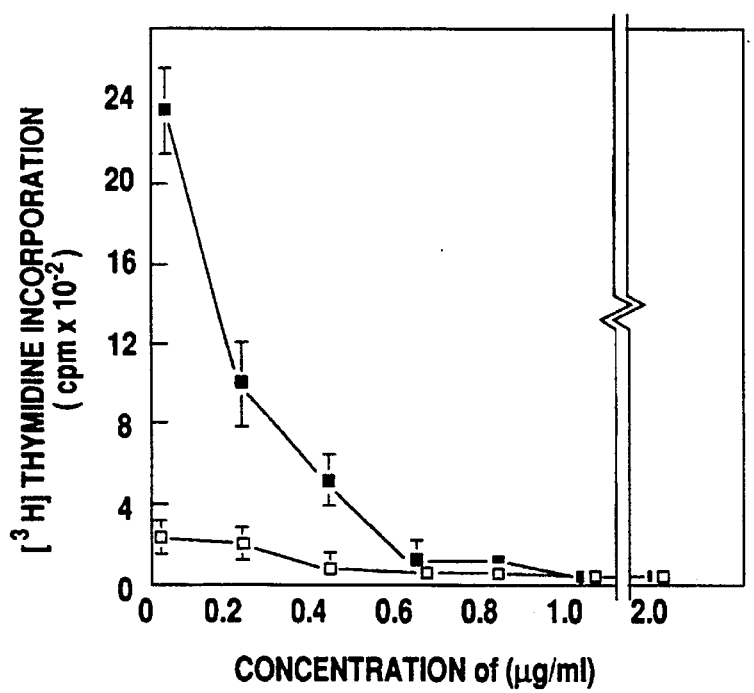
FIG. 3. Inhibitory effect of $T_2$ on IL-2 production. T cells ($1\times10^5$/well) were cultured with medium (□) or PHA (■) in the presence or absence of varying concentrations of $T_2$ for 36 hrs. The cell-free supernatants were diluted 1:4 and analyzed for IL-2 activity with CTLL-2 cells. Mean [$^3$H]-TdR incorporation ± SEM of CTLL-2 cells from 6 experiments is shown.

These studies demonstrate that $T_2$ caused concentration dependent inhibition of PHA induced $^3$H-thymidine incorporation by purified human T lymphocytes (FIG. 1). Fifty percent inhibition was noted at concentrations of approximately 0.2 μg per ml. Cell cycle analysis indicated that $T_2$ prevented cells from progressing through the G1 phase of the cell cycle (FIG. 2). Mitogen induced IL-2 production by purified T-cells was also inhibited by a similar concentration of $T_2$ (FIG. 3). Mitogen induced expression of IL-2 receptors was not inhibited by $T_2$ (Table I) indicating that it was nontoxic to this cellular activity. These results suggested that the decrease in proliferation might be the result of inhibition of IL-2 production.

TABLE 1

EFFECT OF $T_2$ ON INTERLEUKIN-2 (IL-2) RECEPTOR EXPRESSION*

| $T_2$ | Nil | | PHA | |
|---|---|---|---|---|
| | % positive | Fluorescence intensity | % positive | Fluorescence intensity |
| 0 μg/ml | 10 ± 2 | 483 ± 18 | 65 ± 17 | 561 ± 166 |
| 0.65 μg/ml | — | — | 60 ± 22 | 519 ± 109 |
| 1.25 μg/ml | 9 ± 2 | 504 ± 29 | 61 ± 20 | 525 ± 128 |
| 2.50 μg/ml | — | — | — | — |

*T cells (1 × 10$^5$/well) were cultured with medium or phytohemagglutinin (PHA) in the presence or absence of various concentrations of $T_2$ as indicated for 36 hours. Cells were collected, stained with anti-Tac monoclonal antibody followed by fluorescein isothiocyanate-conjugated goat anti-mouse IgG, and analyzed by flow cytometry. Values are the mean ± SEM of 6 experiments.

Figure 4:
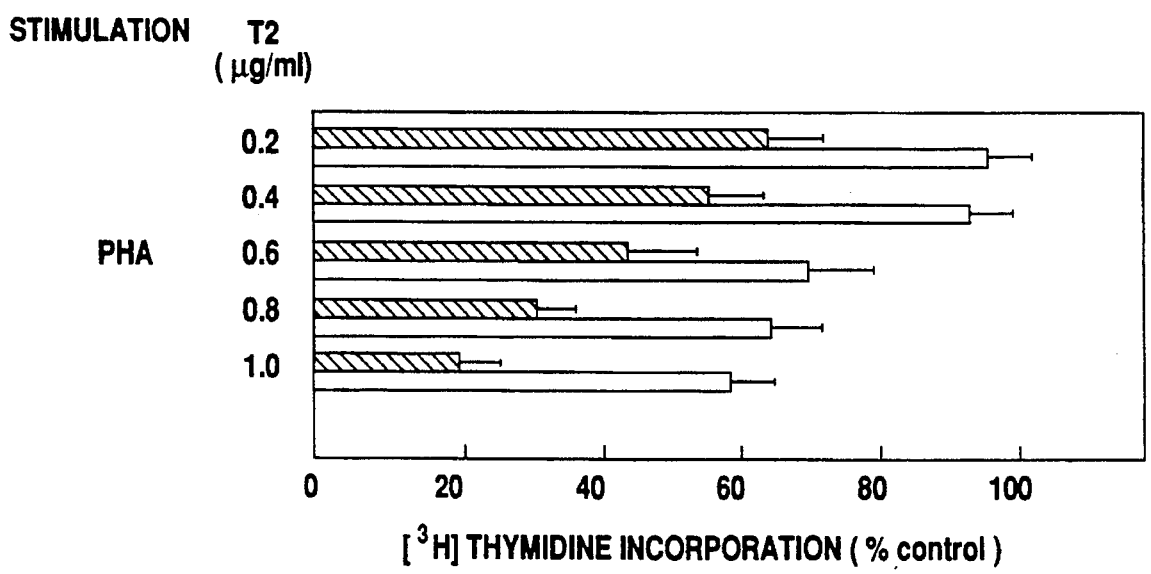
FIG. 4. Effect of supplemental IL-2 on $T_2$ mediated inhibition of T cell proliferation. T cells ($1\times10^5$/well) were stimulated with PHA with (□) or without (■) IL-2 (10 U/ml) and in the presence or absence of varying concentrations of $T_2$ for 3 days. The data are expressed as percent of control [$^3$H]-TdR incorporation from three experiments.
Figure 5:
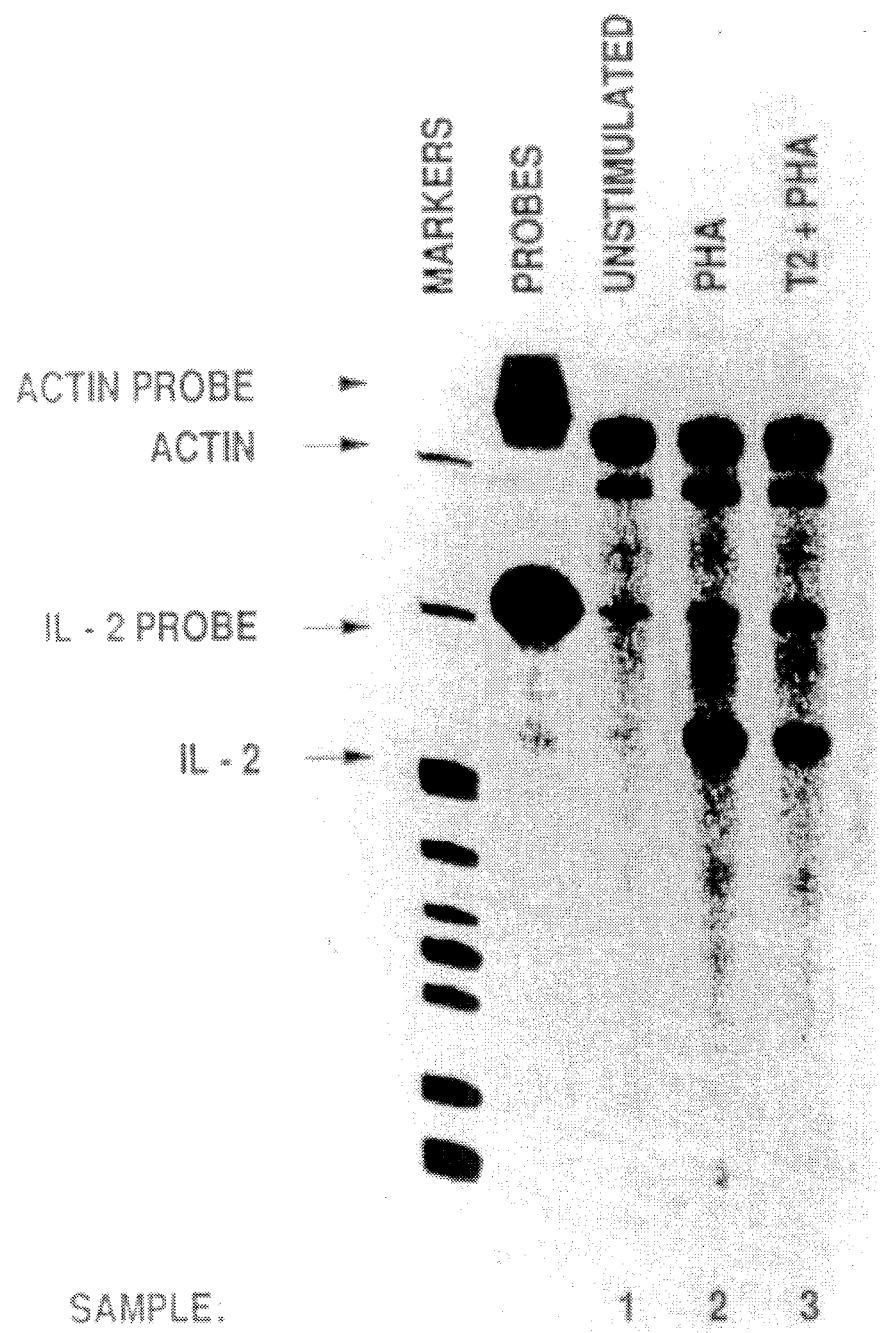
FIG. 5. Effect of $T_2$ on steady state levels of IL-2 mRNA in mitogen stimulated T cells. T cells ($1\times10^6$/ml) were cultured with and without PHA in the presence or absence of $T_2$ (1 µg/ml). After a 4-hour incubation, total RNA was isolated and IL-2 and actin mRNA levels determined by S1 nuclease protection as described[54].

In order to examine IL-2 production, experiments were carried out in which the effect of $T_2$ on proliferation was examined in the presence of supplemental IL-2. As can be seen in FIG. 4, much of the inhibitory effect of $T_2$ was overcome by supplemental IL-2. These results suggested that one of the major actions of $T_2$ was to inhibit IL-2 production. This appeared to result from an inhibition of IL-2 gene transcription since $T_2$ inhibited the appearance of mRNA for IL-2, as shown in FIG. 5. These experiments confirmed that one action of $T_2$ was to inhibit IL-2 production.

A method of testing for selective inhibition of IL-2 specific mRNA production is described herein, the method consists of: culturing eukaryotic cells in culture with and separately without *Tripterygium wilfordii* Hook F $T_2$ extract or components thereof in a therapeutically effective amount to provide a test sample and a control sample; measuring IL-2 mRNA level and a reference mRNA level such as actin mRNA to provide a test IL-2 mRNA sample, a test reference mRNA sample, a control IL-2 mRNA sample and a control reference mRNA sample; comparing (test IL-2 mRNA level ÷ control IL-2 mRNA level) to (test reference mRNA level ÷ control reference mRNA level); and when (test IL-2 mRNA level ÷ control IL-2 MRNA level) is substantially less than 1 and (test reference mRNA level ÷ control reference mRNA level) is about 1, selective inhibition of IL-2 mRNA production by $T_2$ is indicated.

Effect of $T_2$ on Human B Lymphocyte Responses.

Figure 6A:
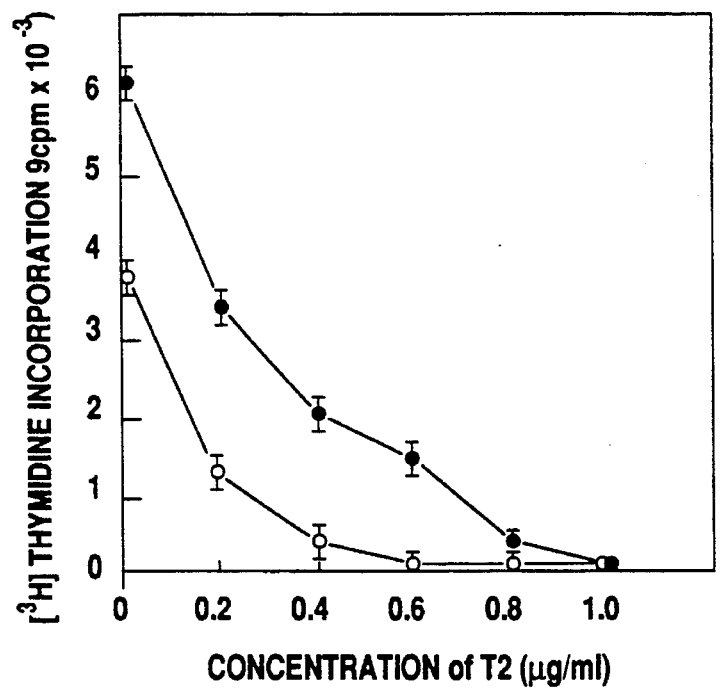
FIGS. 6A–6B. Effect of $T_2$ on B cell DNA synthesis and Ig production.
Figure 6B:
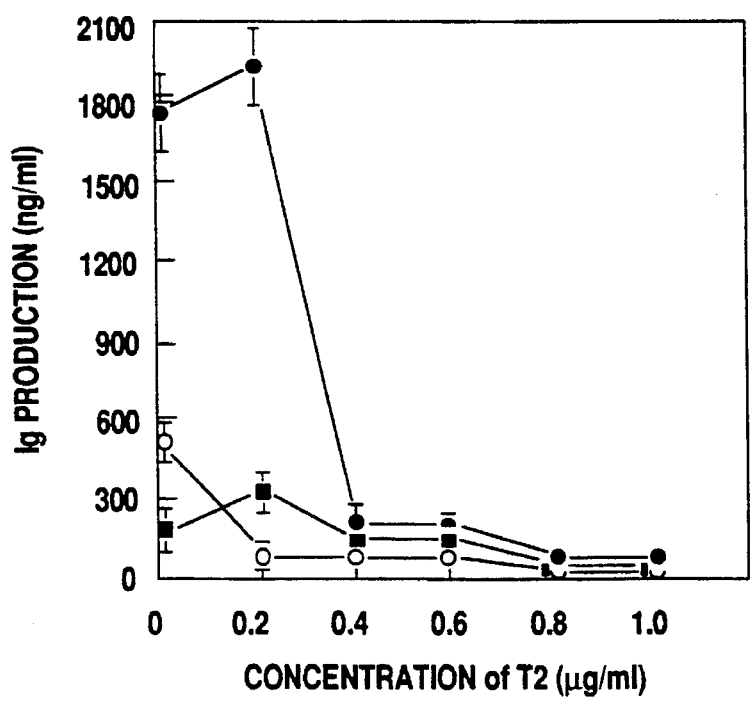

Additional effects of $T_2$ were demonstrated when its action on human B cell responses was examined. As can be seen in FIGS. 6A and 6B, $T_2$ inhibited both mitogen-induced proliferation of highly purified B cells, as well as immunoglobulin production in a concentration dependent manner. These results suggested that $T_2$ had additional effects beyond altering IL-2 production. Some specificity for the action of $T_2$ was demonstrated, however, when its effects on a number of other cell types were examined. Thus, $T_2$ had no effect on IL-1 production by human monocytes nor on their capacity to function as antigen presenting cells. In addition, there was no effect on the growth of endothelial cells or fibroblasts during a 48 hour culture. None of the inhibitory effects of $T_2$ could be accounted for by non-specific toxicity, as inhibitory concentrations of $T_2$ had no effect on the viability of either resting or stimulated lymphocytes, endothelial cells, fibroblasts, monocytes, or polymorphonuclear leukocytes. These results support the contention that $T_2$ has a limited spectrum of immunosuppressive activity which cannot be accounted for by non-specific toxic effects. Of importance, the capacity of $T_2$ to suppress both IL-2 production by T cells, and proliferation and immunoglobulin production by B cells may explain the action of this agent in patients with RA.

EXAMPLE 2

Effect of $T_2$ on Critical Signaling Pathways

The mechanism by which $T_2$ inhibits IL-2 production is examined in greater detail in the present example. *T. wilfordii* may inhibit a critical signaling pathway involved in inducing transcription of the IL-2 gene. Current information suggests that T cell receptor occupancy leads to activation of tyrosine kinases, followed by stimulation of phospholipase C. This results in production of phosphatidyl inositol trisphosphate and diacylglycerol, that induce increases in intracellular calcium and activation of protein kinase C, respectively[60]. Therefore, additional studies were carried out to examine the possibility that $T_2$ might inhibit one of these signaling pathways.

Methods

Effect of $T_2$ Preparation on Total IP Generation by Activated T Cells.

Fresh T cells (A) or Jurkat cells (B) were labeled with [$^3$H]-myo-inositol overnight in the absence or presence of the indicated concentrations of the *T. wilfordii* preparation obtained by chloroform/methanol extraction was obtained from the supplier source described in Example 1. The cells were washed and incubated with 10 mM LiCl for 5 minutes then activated with PHA for 60 min. The cells were extracted with 0.75 ml of a 1:1 mixture of chloroform and methanol, followed by 0.25 ml of chloroform and 0.25 ml of water. The phases were separated by centrifugation and the water soluble fractions were applied to a 0.25 ml Agl-X8 formate ion exchange column. Total inositol phosphate was eluted with 1.5 ml of 0.1M formic acid and 1M sodium formate. The radioactivity was quantified by scintillation counting. An aliquot of each cell population was also stimulated with PHA for 24 hours and supernatants assayed for IL-2 content using CTLL-2 cells.

Effect of $T_2$ on the Generation of IP Fractions by PHA Activated T Cells.

Jurkat cells were labeled with [$^3$H]-myo-inositol overnight in the presence or absence of various concentrations of $T_2$. Following a 5 minute incubation with 10 mM LiCl, the cells were activated with PHA for 60 min. Water soluble IPs were isolated and quantitated. To accomplish this, the cultures were extracted with 0.75 ml of a 1:1 mixture of chloroform/methanol, followed by 0.25 ml each of chloroform and water. The phases were separated by centrifugation and the water soluble fraction was applied to a 0.25 ml Agl-X8 formate ion-exchange column, and washed extensively with 5 mM cold myo-inositol. IP1, IP2 and IP3 were sequentially eluted with 4 ml of 0.2M ammonium formate plus 0.1M formic acid, 10 ml of 0.4M ammonium formate plus 0.1M formic acid and 10 ml of 1M ammonium formate plus 0.1M formic acid respectively. The radioactivity of the various elution fractions was quantified by scintillation counting.

Effect of $T_2$ on DAG Generation and IL-2 Secretion by PHA Stimulated T Cells.

T cells for each sample were cultured overnight with PHA in the presence or absence of the indicated concentrations of $T_2$. The cell pellets were lysed with a mixture of chloroform and methanol, and fractions separated with 1M NaCl and chloroform. The organic phase was collected and dried under nitrogen. DAG mass in the organic extract was assayed by solubilizing the lipid residues in a mixture of $^{32}P$-$\gamma$-ATP and DAG kinase and phosphatidic acid, incubating at 37° C. for 1 hour during which DAG was quantitatively converted to p-phosphatidic acid. The samples were dried and redissolved in chloroform. The solvent was applied to a silica gel and separated by thin layer chromatography with chloroform/methanol/acetic acid. After visualization with iodine, the spot which contained phosphatidic acid was harvested and radioactivity determined by liquid scintillation counting. An aliquot of cells was also stimulated with mitogen and supernatants harvested after 24 hours and assayed for IL-2 content.

Effect of $T_2$ on Translocation of PKC.

Jurkat cells ($1 \times 10^6$/ml) were incubated overnight with or without $T_2$ at the indicated concentrations. The cells were lysed by sonication and then cytoplasmic and membrane fractions separated by centrifugation. PKC activity in both the cytoplasmic and membrane fraction was assayed using a protein kinase C assay system (Amersham) which employed a synthetic peptide as a phosphate acceptor in the presence of phosphatidylserine, calcium and PMA.

Effect of $T_2$ on Protein Tyrosine Phosphorylation.

Jurkat cells ($3 \times 10^6$) were incubated overnight in the absence or presence of the indicated concentrations of $T_2$. The cells were washed and stimulated with PHA for 30 minutes. After centrifugation, the pelleted cells were solubilized with 1 x SDS sample buffer containing protease inhibitors. The lysates were centrifuged at 10,000 rpm for 15 minutes. The supernatants were analyzed for protein phosphorylation by western blotting using a mouse monoclonal antibody (Upstate Biotechnology, Inc.) against phosphotyrosine.

Results

The effect of $T_2$ on Mitogen Induced Production of Phosphatidyl Inositol Metabolites.

Figure 7A:
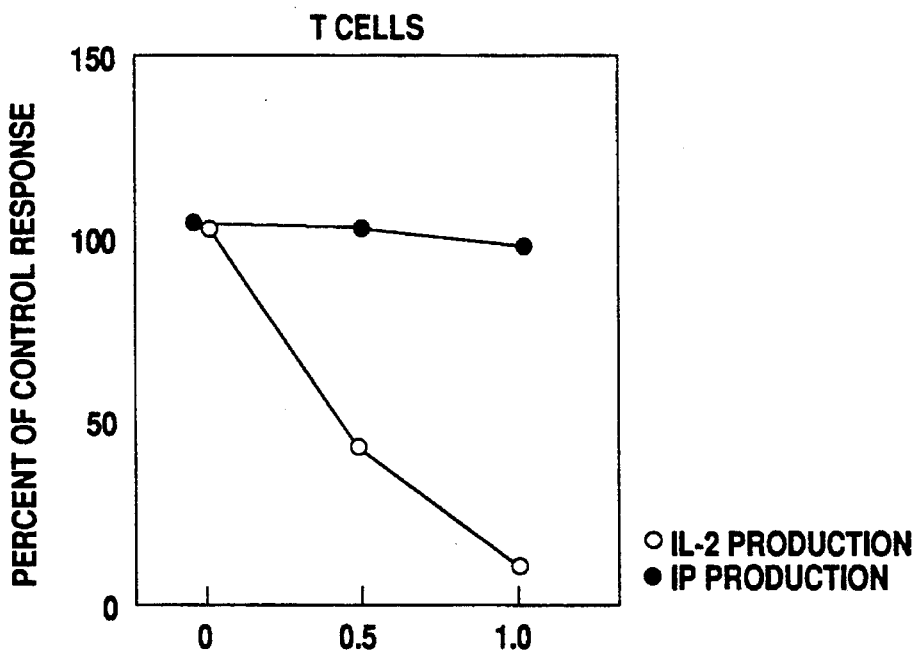
FIGS. 7A–7B. Effect of $T_2$ on total IP generation by activated T cells. Fresh T cells (A) or Jurkat cells (B) were labeled with [$^3$H]-myo-inositol overnight in the absence or presence of the indicated concentrations of $T_2$. Total IP was determined as described in Example 2. An aliquot of each cell population was also stimulated with PHA for 24 hours and supernatants assayed for IL-2 content using CTLL-2 cells (o). Data are the mean of three replicate experiments.
Figure 7B:
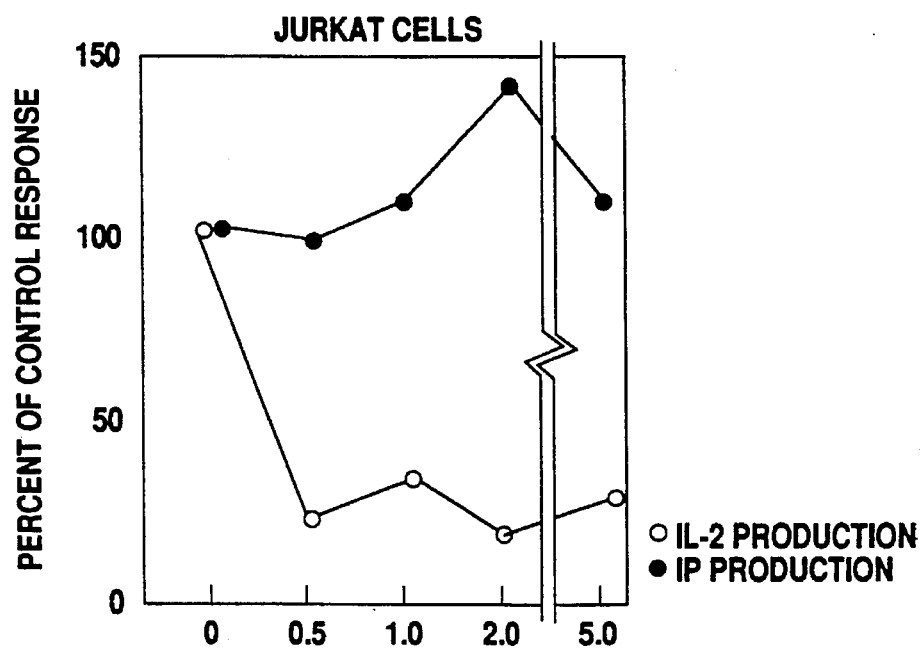
Figure 8A:
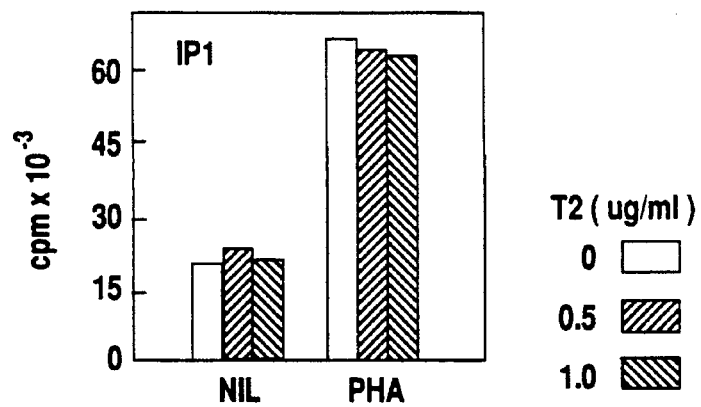
FIGS. 8A–8C. Effect of $T_2$ on the generation of IP fractions by PHA activated T cells. Jurkat cells were labeled with [$^3$H]-myo-inositol overnight in the presence or absence of various concentrations of $T_2$. Following a 5 minute incubation with 10 mM LiCl, the cells were activated with PHA for 60 min. Water soluble IPs were isolated (IP1, FIG. 8A; IP2, FIG. 8B and IP3, FIG. 8C) and quantitated as described in Example 2. Data are from one of three similar experiments.
Figure 8B:
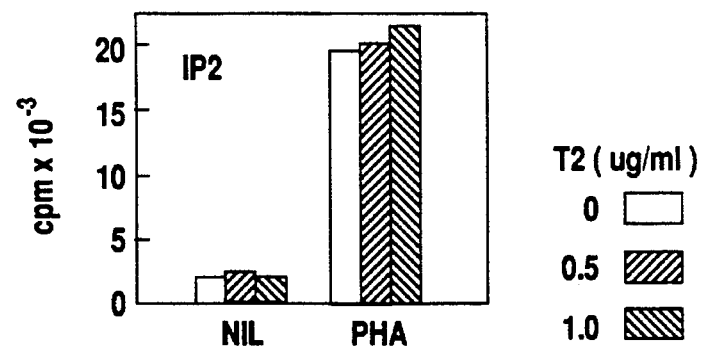
Figure 8C:
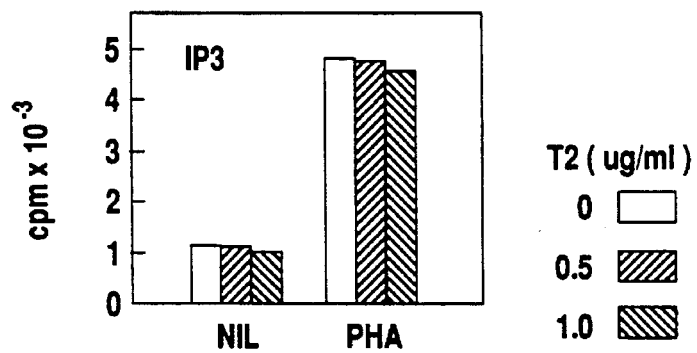
Figure 9:
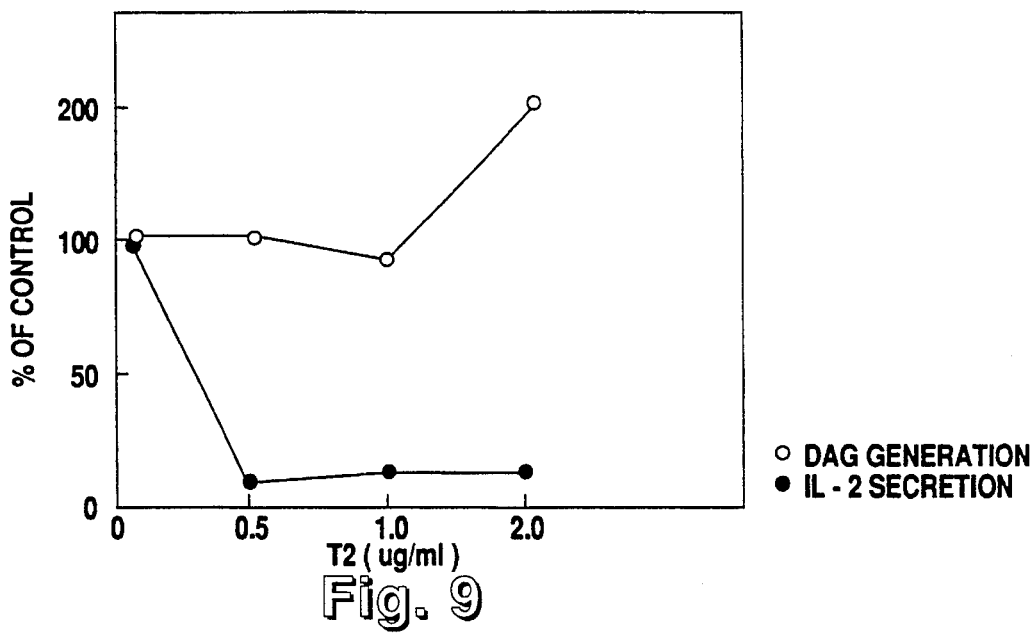
FIG. 9. Effect of $T_2$ on DAG generation and IL-2 secretion by PHA stimulated T cells. DAG and IL-2 were assayed as described in Example 2. Data represent the mean of duplicate determination of three similar experiments.

As can be seen in FIGS. 7A–7B, mitogenic stimulation lead to the production of IL-2 and phosphatidyl inositol metabolites. Whereas IL-2 production was inhibited, generation of phosphatidyl inositol metabolites was not. Similar results were seen in fresh T cells and in the Jurkat leukemic T cell line. Additional studies examined whether $T_2$ specifically inhibited generation of IP3, which is thought to induce increases in intracellular calcium[52]. As can be seen in FIGS. 8A–8C, $T_2$ had no effect on the generation of IP3 or other specific PI metabolites by mitogen activated T cells. Similar experiments examined the effect of $T_2$ on the generation of diacylglycerol. As can be seen in FIG. 9, $T_2$ inhibited IL-2 production from mitogen stimulated T cells, but had no effect on DAG production. Additional of the inventors studies, not shown, examined the activity of $T_2$ on phospholipase C activity isolated from fresh T cells or Jurkat cells. Again, no inhibitory activity was observed. These experiments suggested that the action of $T_2$ cannot be explained by an effect on these early signaling pathways. At these levels of $T_2$ extract addition, nontoxicity to other cellular functions is established as indicated by these cellular assays.

The effect of $T_2$ on Protein Kinase C Activation.

Figure 10A:
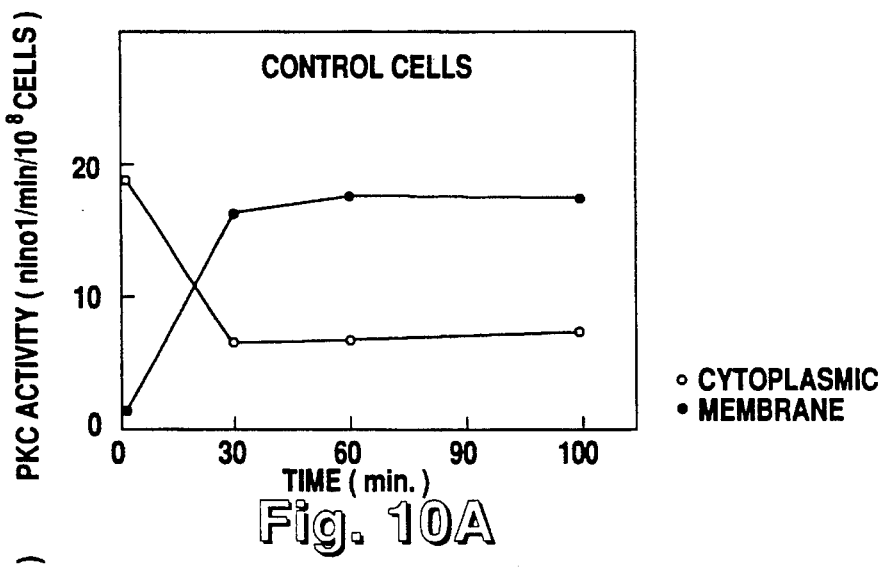
FIGS. 10A–10B. Effect of $T_2$ on translocation of PKC. PKC activity in both the cytoplasmic (FIG. 10A) and membrane (FIG. 10B) fractions were assayed as described in Example 2.
Figure 10B:
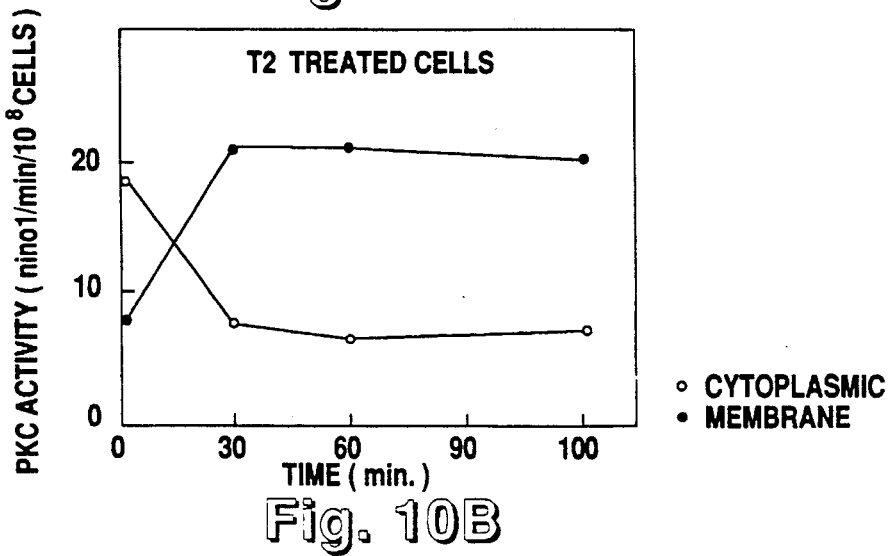
Figure 11:
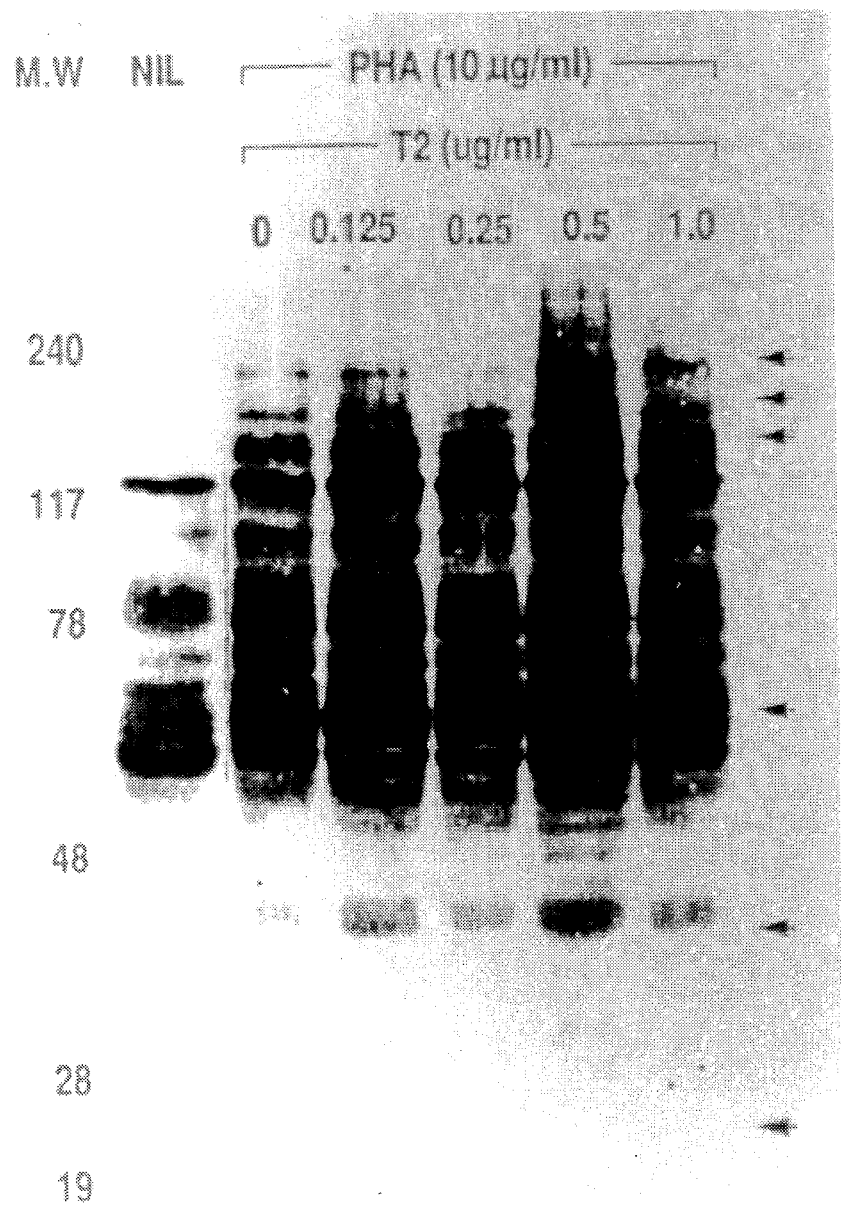
FIG. 11. Effect of $T_2$ on protein tyrosine phosphorylation. See Example 2 for methods. Arrows indicate tyrosine phosphorylation of new proteins after PHA stimulation.

As can be seen in FIGS. 10A–10B, mitogen stimulation led to translocation of PKC in Jurkat cells, and $T_2$ did not effect PKC translocation. Finally, the effect of $T_2$ on the activity of protein tyrosine kinase activity was explored. As can be seen in FIG. 11, mitogenic stimulation of T cells lead to phosphorylation of a number of protein species identified with a specific antibody to phosphotyrosine. However, $T_2$ did not inhibit the activity of protein tyrosine kinase since the same bands were observed regardless of the presence of $T_2$ during mitogenic stimulation. These experiments convincingly demonstrate that $T_2$ has no effect on early signaling pathways involved in induction of IL-2 gene transcription.

EXAMPLE 3

In Vivo Trials

In an open trial, it was found that a mixture of compounds ($T_2$) extracted from *Tripterygium wilfordii* Hook F was effective in the treatment of rheumatoid arthritis.

To confirm the previous results obtained from these open studies, a prospective, controlled, double-blind cross-over study was designed and carried out in the outpatient clinic of Dr. Tao in Beijing, People's Republic of China.

The treatment plan was designed as follows:

Seventy patients with classic or definite adult-onset rheumatoid arthritis who had active disease for more than 6 months were accepted into the trial and randomly assigned to 2 treatment groups. Patients in Group A received $T_2$ for a first course of treatment of 12 weeks, and then were subsequently changed to placebo for a second course of treatment of 4 weeks duration. Patients of Group B received placebo during the first course and then were crossed-over and received $T_2$ therapy during the second course. $T_2$ was taken in a dosage of 60 mg daily. Placebo tablets were identical in appearance to $T_2$ tablets. Table 2 shows the treatment plan schedule.

TABLE 2

| TREATMENT PLAN (TOTAL COURSE: 16 WEEKS) | | |
|---|---|---|
| | First course treatment (12 weeks) | Second course treatment (4 weeks) |
| Group A | $T_2$, 20 mg t.i.d. | Placebo |
| Group B | Placebo | $T_2$, 20 mg t.i.d. |

All patients were assessed in an arthritis clinic every 4 weeks. The clinical assessment, overall assessment by physicians and drug distribution were carried out by individual doctors in a blinded manner. The laboratory assessments were done by technicians of a central hospital laboratory, who were also blinded to the details of the trial.

TABLE 3

CLINICAL FEATURES OF PATIENTS ENTERING THE TRIAL

| | First Treatment Course | | Second Treatment Course | |
|---|---|---|---|---|
| | Group A $T_2$ | Group B Placebo | Group A Placebo | Group B $T_2$ |
| Number of Patients | 35 | 35 | 27 | 31 |
| Male/Female | 3/32 | 4/31 | 1/26 | 4/27 |
| Mean age, years | 46.3 | 48.0 | 46.2 | 47.7 |
| Mean disease duration (years) | 5.9 | 6.1 | 5.8 | 6.0 |
| Stage of Disease | | | | |
| (1) | 6 | 6 | 4 | 5 |
| (2) | 14 | 16 | 11 | 13 |
| (3) | 12 | 10 | 10 | 9 |
| (4) | 3 | 3 | 2 | 4 |

The clinical features of patients entering the trial are shown in Table 3. Statistical analyses demonstrated that at the beginning of the trial, Group A and Group B did not differ from each other significantly in age, sex, duration of disease or stage of disease.

TABLE 4

RESULTS OF A CONTROLLED TRIAL OF $T_2$ IN RHEUMATOID ARTHRITIS

| | | No. of Patients Completing Treatment | |
|---|---|---|---|
| Group | No. Beginning Treatment | First Course (12 wks) | Second Course (4 wks) |
| A ($T_2$ —> Placebo) | 35 | 27 | 24 |
| B (Placebo —> $T_2$) | 35 | 31 | 25 |

As shown in Table 4, 27 patients of Group A completed the first course of treatment, of which 24 completed the second course. 31 and 25 of Group B completed the first course and second course of treatment, respectively.

Table 5 indicates the reasons patients withdrew from the study. Three patients of Group B but none of Group A withdrew from the trial because of worsening of disease during the first course of treatment, whereas 4 patients from Group A but none from Group B withdrew from the trial because of side effects.

TABLE 5

REASONS FOR WITHDRAWAL FROM THE STUDY

| | First Course Treatment | | | | Second Course Treatment | | | |
|---|---|---|---|---|---|---|---|---|
| | Group A $T_2$ (n = 35) | | Group B Placebo (n = 35) | | Group A Placebo (n = 27) | | Group B $T_2$ (n = 31) | |
| | No. | % | No. | % | No. | % | No. | % |
| Lost to follow up | 4 | 11 | 1 | 3 | 3 | 11 | 6 | 19 |
| Worsening of disease | 0 | 0 | 3 | 9 | 0 | 0 | 0 | 0 |
| Side effects | 4 | 11 | 0 | 0 | 0 | 0 | 0 | 0 |

Table 6 shows the therapeutic effects of the first course of treatment. In comparison with patients of Group B, patients of Group A showed significant improvement in all clinical assessments including morning stiffness, joint tenderness score, number of swollen joints, grip strength and 15 meter walking time.

TABLE 6

CHANGES IN CLINICAL PARAMETERS IN PATIENTS COMPLETING THE FIRST COURSE OF TREATMENT

| | | Group A $T_2$ (n = 27) | Group B Placebo (n = 31) | *p |
|---|---|---|---|---|
| Morning stiffness (hours) | Before | 2.4 ± 0.4 | 1.1 ± 0.2 | 0.01 |
| | After | 0.9 ± 0.2 | 2.3 ± 1.4 | |
| Joint tenderness score | Before | 25.1 ± 1.9 | 25.5 ± 1.7 | 0.001 |
| | After | 7.9 ± 1.3 | 21.9 ± 2.1 | |
| Number of swollen joints | Before | 9.2 ± 0.9 | 7.8 ± 0.7 | 0.01 |
| | After | 4.3 ± 0.6 | 7.4 ± 1.1 | |
| Grip strength (mean of both sides, mm Hg) | Before | 49.0 ± 0.4 | 73.6 ± 7.7 | 0.05 |
| | After | 84.4 ± 7.5 | 81.2 ± 8.9 | |
| 15 meter walking time (second) | Before | 36.6 ± 6.6 | 37.0 ± 2.4 | 0.05 |
| | After | 21.6 ± 1.5 | 31.9 ± 3.6 | |

The most noteworthy improvement was observed in joint tenderness score, which improved from a mean of 25.1 before entry to a mean of 7.9 after the first course of treatment with $T_2$. By contrast, there were no significant changes in this score in Group B patients treated with placebo.

As shown in Table 7, treatment with $T_2$ also caused improvement in laboratory correlates of disease activity. Significant improvements in ESR, CRP and immunoglobulin levels were noted. The changes were significant at the p 0.001 level when compared between Group A and Group B.

TABLE 7

CHANGES IN LABORATORY PARAMETERS IN PATIENTS COMPLETING THE FIRST COURSE OF TREATMENT

| | | Group A $T_2$ (n = 27) | Group B Placebo (n = 31) | *p |
|---|---|---|---|---|
| ESR (mm/hour) | Before | 69.2 ± 6.4 | 63.9 ± 5.2 | <0.001 |
| | After | 41.0 ± 5.9 | 67.2 ± 6.6 | |
| CRP (u/ml) | Before | 29.4 ± 5.7 | 31.6 ± 4.1 | <0.001 |
| | After | 10.4 ± 3.9 | 43.7 ± 7.0 | |
| RF (titers) | Before | 87.1 ± 23.2 | 86.1 ± 35.5 | NS |
| | After | 48.0 ± 13.4 | 63.4 ± 10.9 | |
| IgG (u/ml) | Before | 227.5 ± 4.6 | 231.9 ± 14.2 | <0.001 |
| | After | 117.4 ± 9.5 | 180.4 ± 29.8 | |
| IgM (u/ml) | Before | 302.8 ± 40.3 | 284.5 ± 32.2 | <0.001 |
| | After | 105.2 ± 11.1 | 261.3 ± 29.3 | |
| IgA (u/ml) | Before | 289.6 ± 29.4 | 257.6 ± 25.2 | <0.001 |
| | After | 149.0 ± 15.5 | 280.4 ± 29.8 | |

*Group A vs Group B

There was a greater tendency to decrease RF titer in $T_2$ treated patients but the difference between the two groups after the first course of treatment was not statistically significant.

During the second course of therapy, patients who had received placebo initially improved significantly after 4 weeks of therapy with $T_2$. (See Table 8). Significant improvements in joint tenderness score, number of swollen joints and grip strength were noted. Improvement in morning stiffness and 15 meter walking time were also noted, but these changes did not achieve statistical significance. Patients who had received $T_2$ during the first 12 weeks of therapy continued to maintain improvement even after 4 weeks of placebo therapy during the second course.

TABLE 8

CHANGES IN CLINICAL PARAMETERS IN PATIENTS COMPLETING THE SECOND COURSE OF TREATMENT

| | | Group A $T_2$ (n = 27) | *p | Group B Placebo (n = 31) | *p |
|---|---|---|---|---|---|
| Morning stiffness (hours) | Before | 1.8 ± 0.2 | NS | 2.5 ± 1.7 | NS |
| | After | 0.8 ±0 0.2 | | 1.3 ± 0.9 | |
| Joint tenderness score | Before | 7.9 ± 1.4 | NS | 22.2 ± 2.4 | <0.001 |
| | After | 11.0 ± 2.6 | | 13.5 ± 2.0 | |
| Number of swollen joints | Before | 4.2 ± 0.8 | NS | 7.0 ± 1.2 | <0.05 |
| | After | 4.4 ± 0.9 | | 3.5 ± 0.5 | |
| Grip strength (mean of both sides, mm Hg) | Before | 87.5 ± 8.0 | <0.05 | 80.1 ± 9.2 | 0.05 |
| | After | 70.2 ± 9.5 | | 97.1 ± 13.2 | |
| 15 meter walking time (second) | Before | 20.3 ± 1.7 | NS | 31.5 ± 5.9 | NS |
| | After | 17.1 ± 0.6 | | 18.9 ± 2.3 | |

*After vs before treatment

Aside from grip strength, no significant changes were observed in clinical assessments in Group A patients after 4 weeks of placebo treatment.

As shown in Table 9, significant decreases in ESR and RF titer were noted in Group B patients after the second course of treatment. No significant worsening in laboratory parameters were noted in Group A patients after 4 weeks of placebo therapy.

TABLE 9

CHANGES IN LABORATORY PARAMETERS IN PATIENTS COMPLETING THE SECOND COURSE OF TREATMENT

| | | Group A $T_2$ (n = 24) | | Group B Placebo (n = 25) | *p |
|---|---|---|---|---|---|
| ESR (mm/hour) | Before | 42.3 ± 6.0 | NS | 68.5 ± 6.9 | <0.001 |
| | After | 31.7 ± 7.3 | | 22.0 ± 4.9 | |
| RF (titers) | Before | 49.3 ± 13.5 | NS | 67.2 ± 12.1 | <0.05 |
| | After | 32.0 ± 12.3 | | 32.0 ± 19.1 | |

*After vs before treatment

The overall effectiveness of $T_2$ in the present trial was classified by its capacity to induce remissions, meaningful improvement or no therapeutic effect. (See Table 10).

TABLE 10

OVERALL EVALUATION OF THE PRESENT TRIAL

| | First Course Treatment | | | | Second Course Treatment | | | |
|---|---|---|---|---|---|---|---|---|
| | Group A $T_2$ (n = 27) | | Group B Placebo (n = 31) | | Group A Placebo (n = 24) | | Group B $T_2$ (n = 25) | |
| | No. | % | No. | % | No. | % | No. | % |
| Remission | 2 | 7.4 | 0 | 0 | 0 | 0 | 0 | 0 |
| Improvement Patient's assessment | 25 | 93 | 7 | 23 | 20 | 82 | 20 | 80 |
| Physician's assessment | 25 | 93 | 7 | 23 | 19 | 79 | 22 | 88 |
| Clinical criteria | 22 | 82 | 7 | 23 | 19 | 79 | 11 | 44 |
| Laboratory evaluation | 23 | 85 | 4 | 13 | 18 | 75 | 13 | 52 |

Based on the therapeutic criteria for remission in RA developed by a subcommittee of the ARA, remission was observed in two patients of Group A at the end of the first course of treatment.

The percentage of patients who experienced meaningful improvements was significantly higher for Group A than for Group B patients as evaluated by physician's assessment, and clinical and laboratory evaluations after the first course of treatment.

The percent of Group B patients experiencing meaningful improvement after the second course of treatment was also remarkable, whereas improvement was maintained in Group A patients during the 4 week second course of placebo.

In order to determine whether $T_2$ exerted an immunosuppressive effect in patients with RA, peripheral blood mononuclear cells (PBMC) were obtained from 18 patients of each group before and after the first course of treatment. These cells were cultured for 14 days and the amounts of IgM-RF and total IgM secreted were determined using a radioimmunoassay. (See Table 11).

TABLE 11

PRODUCTION OF IgM-RF AND TOTAL IgM BY PBMC OF PATIENTS AFTER THE FIRST COURSE OF TREATMENT

| | | Group A $T_2$ (n = 18) | Group B Placebo (n = 18) | *p |
|---|---|---|---|---|
| RF | Before | 7.2 ± 3.2 | 5.4 ± 1.6 | <0.01 |
| | After | 1.5 ± 0.5 | 7.0 ± 2.2 | |
| IgM | Before | 220.7 ± 53.6 | 260.5 ± 49.3 | <0.01 |
| | After | 151.9 ± 55.3 | 301.2 ± 100.5 | |

*Group A vs Group B

In comparison with Group B, significant decreases in both IgM-RF and total IgM were noted in Group A after $T_2$ treatment. These results suggest that $T_2$ therapy had suppressed both IgM and IgM RF production in these patients and thus exerted an immunosuppressive effect.

As shown in Table 12, the most common side effects of $T_2$ were dermal reactions including skin rash, cheilosis, thinning of skin and nails and pigmentation.

TABLE 12

INCIDENCE OF ADVERSE REACTIONS

|  | First Course Treatment | | | | Second Course Treatment | | | |
| --- | --- | --- | --- | --- | --- | --- | --- | --- |
|  | Group A $T_2$ (n = 31) | | Group B Placebo (n = 31) | | Group A Placebo (n = 24) | | Group B $T_2$ (n = 25) | |
|  | No. | % | No. | % | No. | % | No. | % |
| Skin rash & cheilosis | 15 | 39 | 1 | 3 | 0 | 0 | 7 | 28 |
| Diarrhea | 6 | 27 | 0 | 0 | 0 | 0 | 2 | 8 |
| Anorexia | 2 | 5 | 0 | 0 | 1 | 4 | 0 | 0 |
| Abdominal pain | 2 | 5 | 1 | 3 | 0 | 0 | 0 | 0 |
| Amenorrhea | 5/16 | 31 | 0 | 0 | 5/16 | 31 | 1/18 | 6 |
| Postmenopausal vaginal bleeding | 1/10 | 10 | 0 | 0 | 0 | 0 | 0 | 0 |

Although the incidence of skin reactions was quite high in Group A during the first course of treatment, none of the patients had to discontinue $T_2$ treatment. Amenorrhea was another important side effect of $T_2$. It was observed that 31% of female patients aged 49 or less having received $T_2$ for 12 weeks developed amenorrhea whereas 6% of patients developed it after 4 weeks of $T_2$ treatment. Amenorrhea disappeared in most patients when $T_2$ was discontinued.

Figure 12:
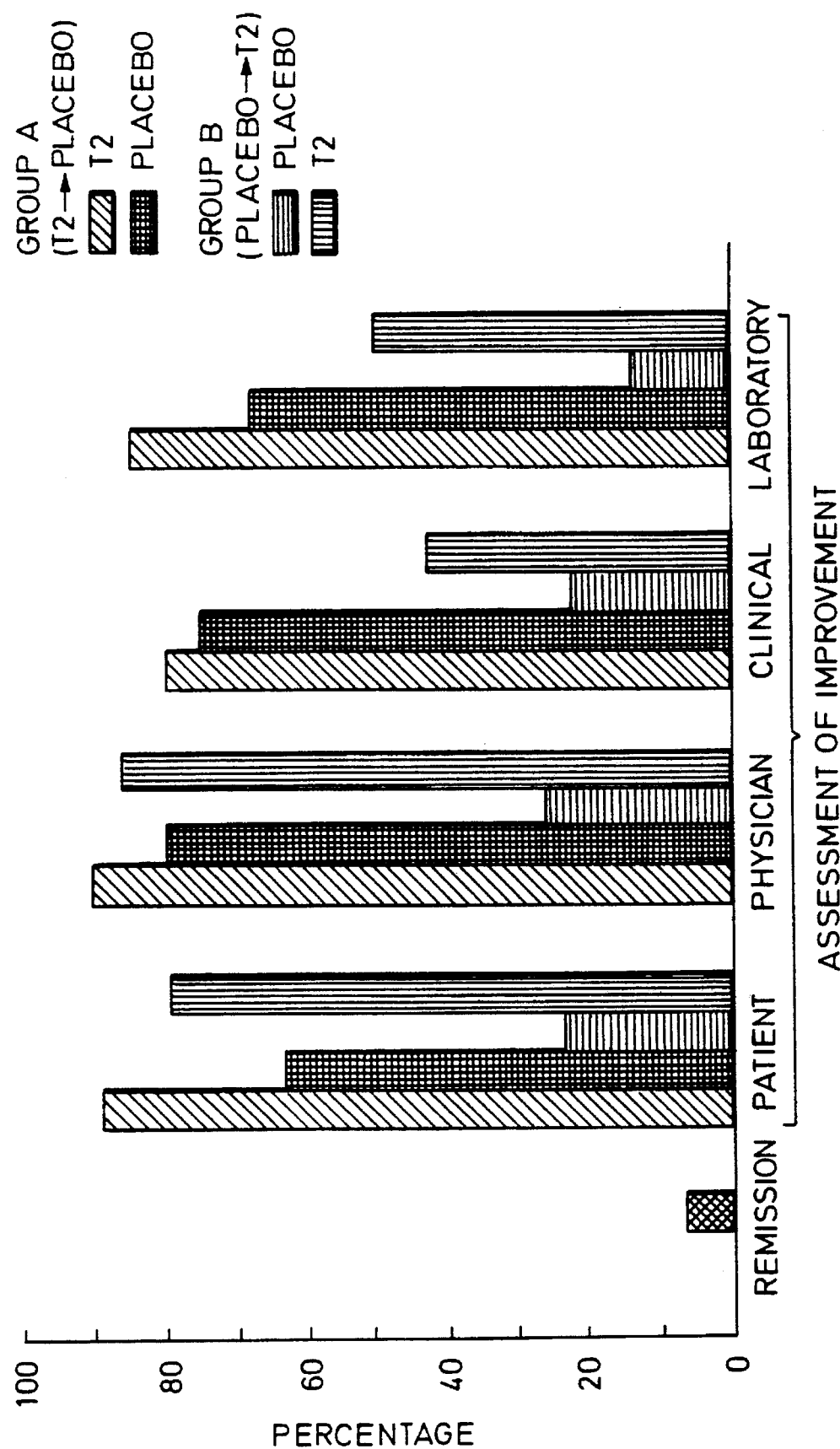
FIG. 12 summarizes assessment of symptomatic improvement in rheumatoid arthritis patients as a result of treatment with a mixture from *Tripterygium wilfordii* Hook F.

FIG. 12 summarizes the assessed improvements in symptoms of rheumatoid arthritis described above. $T_2$ is an effective treatment for rheumatoid arthritis, significantly improving clinical manifestations and laboratory correlates of inflammation. Although toxicity was frequent, it necessitated cessation of therapy in few. Clinical improvement was observed after only 4 weeks of therapy and persisted for at least 4 weeks after the medication was discontinued. Therapy with $T_2$ suppresses the in vitro production of IgM and IgM rheumatoid factor.

Administration of the $T_2$ extract has also been shown to be effective in the treatment of systemic lupus erythematosus (Table 13). It also appears to be effective in relieving acute clinical manifestations including joint inflammation, skin rash and renal disease (Table 13). Asteroid sparing effect of $T_2$ was also noted. In comparison with corticosteroids and commonly used immunosuppressive agents, such as cyclophosphamide, patients treated with $T_2$ had fewer significant complications.

TABLE 13

THERAPEUTIC EFFECT OF $T_2$ IN LUPUS NEPHRITIS

1. Patient group
   10 patients, aged 22–37, with duration of disease > 1 year were treated with $T_2$
2. Laboratory evaluation - before treatment
   +ANA:10
   anti-DNA binding > 20%:9
   Proteinuria > 3 g/24h:10
   Elevated serum creatinine:3
3. Treatment plan:
   First month: $T_2$ 20 mg tid. Maintain prednisone < 40 mg/day
   Followed by $T_2$ 10 mg tid. and tapered prednisone
   Total course of $T_2$:24 weeks
4. Results of treatment:
   Serum creatinine returned to normal in ⅔
   Proteinuria improved in 10/10:
   undetectable:3
   <1 g/24h:3
   >1 g/24h:4

TABLE 13-continued

THERAPEUTIC EFFECT OF $T_2$ IN LUPUS NEPHRITIS

Concomitant Medication

3: withdrew from preunisone
6: continued preunisone <10 mg/day
1: changed to cyclophosphamide

EXAMPLE 4

Components of $T_2$ Extract and Toxicity thereof

The present example is provided to demonstrate the isolation and characterization of the various chemical components of a *T. wilfordii* Hook F root extract identified by the present inventors.

Figure 19:
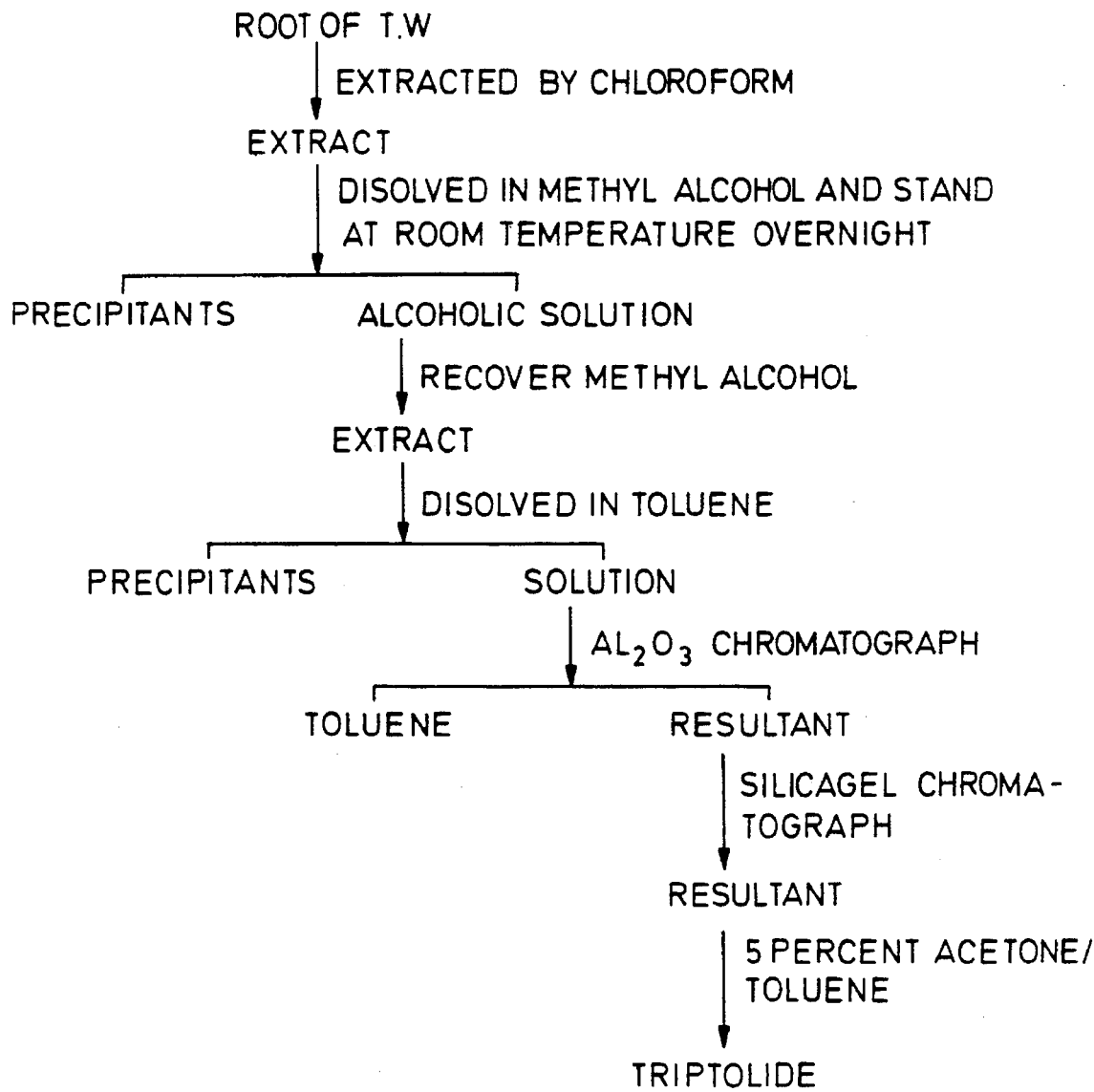
FIG. 19 outlines the extraction procedure for preparation of triptolide.

The structures of triptolide and triptodiolide are shown in FIG. 13. FIG. 14 shows the structure of triptonide. Triptolide was isolated from alcoholic extracts of *Tripterygium wilfordii* Hook F by the method of Kupchan et al.[31]. This scheme for triptolide preparation is outlined in FIG. 19. The present example demonstrates the effects of the $T_2$ extract (described in Example 1) or triptolid on the in cellulo of viability of important immunopotent cells.

The effect of triptolide on immunopotent cells in vitro was determined as follows:

T cells, B cells and fibroblasts ($1 \times 10^6$/ml) were incubated with varying concentrations of $T_2$ or triptolide for 72 hr. The cells were assayed for cell viability by using a cytoflowmeter (FACSCAN) after the cells were stained with propidium iodine. Table 14 demonstrates the effect of $T_2$ or triptolide on cell viability.

TABLE 14

EFFECT OF $T_2$ OR TRIPTOLIDE ON CELL VIABILITY
Inhibitors

| Cell type | Control | $T_2$ (μg/ml) | | | | Triptolide (ng/ml) | | |
| --- | --- | --- | --- | --- | --- | --- | --- | --- |
|  |  | 0.1 | 1.0 | 10.0 | 100.0 | 0.1 | 1.0 | 10.0 |
|  |  | (Percent viable cells) | | | | | | |
| T cells | 91.7 | 90.0 | 89.3 | 88.2 | 18.8 | 29.5 | 29.8 | 11.5 |
| B cells | 55.6 | 50.9 | 44.3 | 30.5 | 10.6 | 20.9 | 20.9 | 15.6 |
| Fibroblasts | 77.5 | 92.7 | 95.1 | 86.6 | 43.0 | 91.7 | 89.3 | 35.8 |

$T_2$ at 100 μg/ml and triptolide at 10 ng/ml were toxic to fibroblasts indicating that at these levels, toxicity is nonspecific. At lower levels, suppression of T cell and B cell function is seen.

The capacity of triptolide to inhibit in vitro responses of human lymphocytes was examined. As can be seen in table 15, triptolide inhibited proliferation of both T and B lymphocytes profoundly at concentrations of 0.1–1.0 ng/ml.

TABLE 15

| Concentration of triptolide (ng/ml) | PHA-Induced T Cell DNA Synthesis | SA-Induced B Cell DNA Synthesis |
| --- | --- | --- |
|  | ($^3$H-Tymidine Incorporation, CPM) | |
| 0 | 93,400 | 7,900 |
| 0.1 | 24,200 | 2,000 |
| 1.0 | 100 | 100 |

Figure 16:
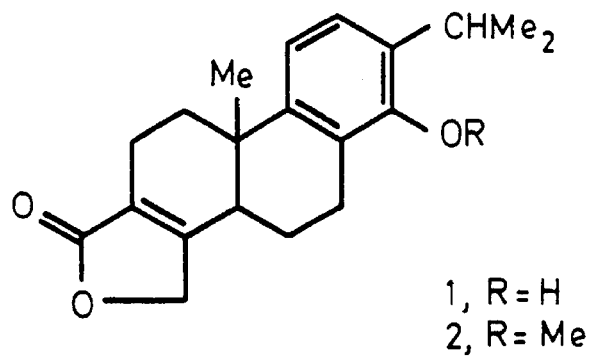
FIG. 16 shows the structure of triptophenolide (1) and triptophenolide methyl ester (2).
Figure 17:
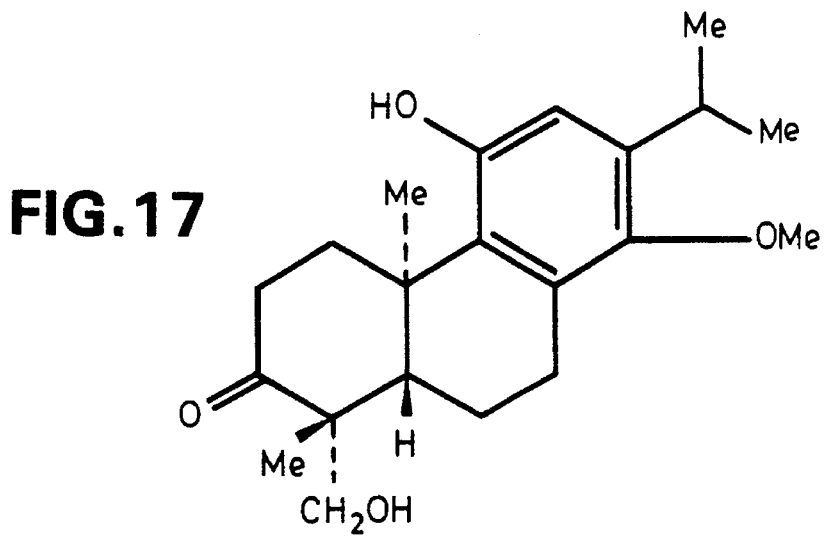
FIG. 17 schematically shows the structure of triptonoterpenol.
Figure 18:
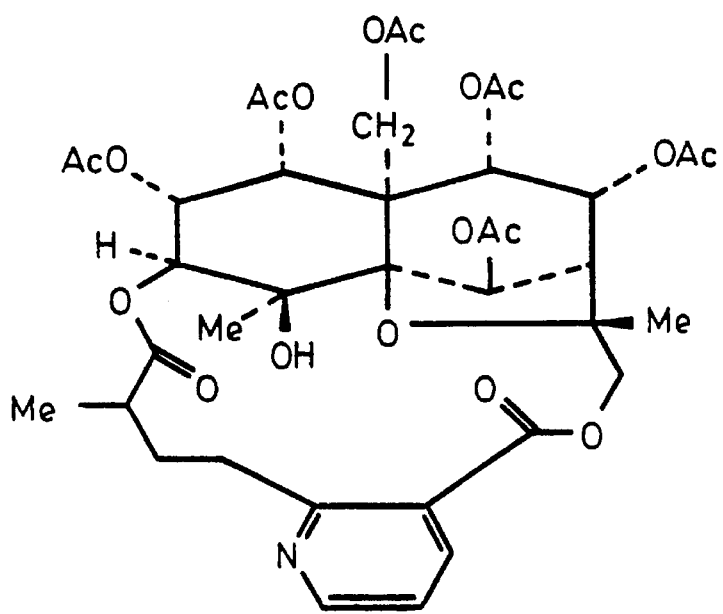
FIG. 18 schematically shows the structure of wilformine.

Additional studies indicated that this triptolide fraction also inhibited the in vitro production of immunoglobulin from mitogen stimulated human B lymphocytes at comparably small concentrations. These results demonstrate that the triptolide fraction is extremely toxic, however, its specificity of action is yet to be determined. Other components of *Tripterygium wilfordii* Hook F include:

- polpunonic acid (wilfortrine) (1) and the methyl ester thereof (2) shown in FIG. 15 and described by Keng et al. (Chem. Abst. 107:55718y, p436, 1987);
- triptophenolide (1) and triptophenolide methyl ether (2) shown in FIG. 16 and described by Wu et al. (Chem. Abst. 107:96917f, p712, 1987);
- triptonoterpenol shown in FIG. 17 and described by Deng et al. (Chem. Abst. 107:112684k, p112692, 1987); and
- wilformine (shown in FIG. 18), wilforine, wilforgine, and wilforzine described by He et al. (Chem. Abst. 107:130906p, 1987;

Purified components of the *T. wilfordii* extract that have reduced concentrations of triptolide will be administered to patients with autoimmune and inflammatory diseases including rheumatoid arthritis, systemic lupus erythematosus and psoriasis. Dosage will be determined based on the concentration of each therapeutic component in the T. mixture. After phase I dosage, escalation studies will be carried out to evaluate toxicity. Trials with non-toxic doses will be carried out to determine efficacy.

EXAMPLE 5

Ethyl Acetate Preparation of *Tripterygium wilfordii* Hook F

The present example is provided to demonstrate that the preparation of *Tripterygium wilfordii* Hook F may be obtained using a variety of extraction protocols, including extraction by ethyl acetate.

An extract of the *Tripterygium wilfordii* Hook F root was prepared employing an ethyl acetate extraction protocol. This preparation is described as part of the present invention as a Texas ethyl acetate (TEA) preparation. It is proposed that the TEA will be administered orally in clinical use.

To prepare the TEA extract, roots of TWH obtained from Fujian Province of China were peeled and dried in the open air and in the sunlight. The plant wood may also be dried using other techniques including a low heat oven or incubator that will reach temperatures of at least about 60° C. The woody parts of the root were ground to a powder. One thousand grams of the coarse powder of TWH were extracted with 2500 ml of 95% ethanol for 24 hours. The extracted material was collected in 5000 ml of 95% ethanol. The plant residue was refluxed with 95% ethanol for 2 hours and the ethanol extract was combined with the initial extract. The combination was evaporated under reduced pressure until all ethanol was removed. The concentrated ethanol extract was dissolved in ethyl acetate with the aid of ultrasonification. The ethyl acetate extract was filtered and the residue was dissolved with ethyl acetate repeatedly. The ethyl acetate extract was combined, filtered and evaporated to dryness under reduced pressure. The material was ground into a fine powder and mixed with starch. The mixed powder was further screened through a #60 sieve. This mixture will be incorporated into capsules suitable for human use using techniques well known to those of ordinary skill in the art[61] (see Remington's Pharmaceutical Sciences, 18th ed. (1990) for clinical trials which reference is specifically incorporated herein by reference for this purpose. One tablet will contain 30 mg of the TEA extract. The TEA extract contains little triptolide, and the tablets will contain preferably no more than 10 μg to 20 μg of triptolide. Triptolide was measured with HPLC by comparison with a known standard of triptolide as described in Example 4 and FIG. 19. A single batch of 1400 gm was prepared and utilized for the pre-clinical evaluation described below.

Figure 23:
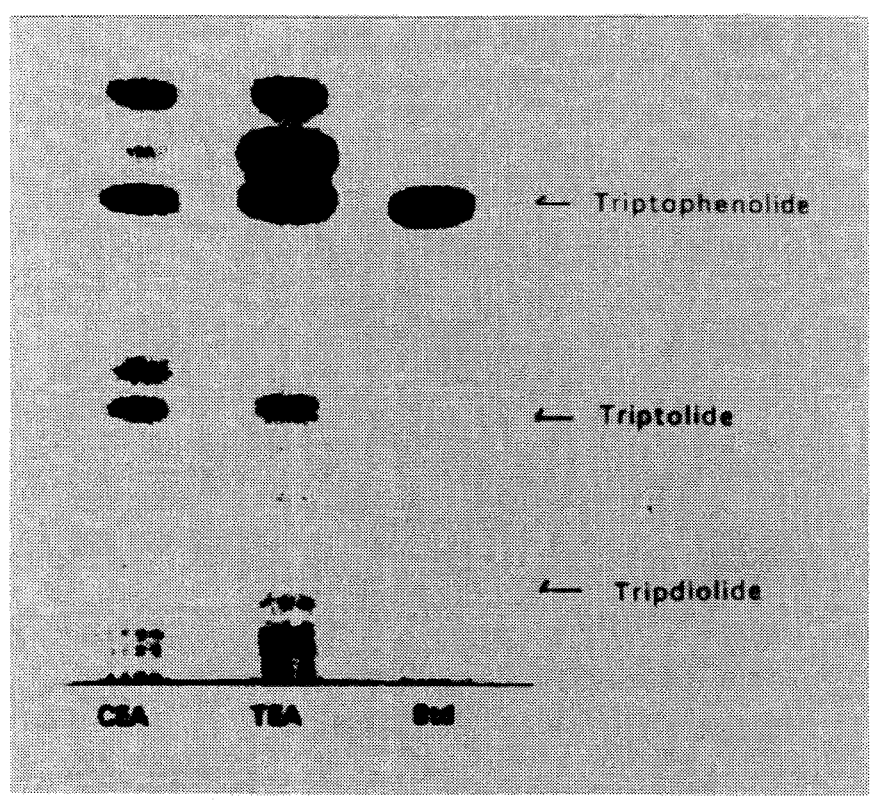
FIG. 23. Comparison of the diterpenes in the ethyl acetate extracts of *Tripterygium wilfordii* Hook F prepared in China (CEA) and Texas (TEA). TEA is an ethyl acetate extract of *Tripterygium wilfordii* Hook F prepared at UT Southwestern Medical Center at Dallas. CEA is an ethyl acetate extract of *Tripterygium wilfordii* Hook F prepared in China. The diterpenes of each *T. wilfordii* Hook F preparation (CEA and TEA) were visualized by the Kedde reaction. Triptolide (3.6 µg), triptophenolide (10 µg) and tripdiolide (1.8 µg) served as reference standards. The relative concentrations of triptophenolide, triptolide and tripdiolide of the CEA and TEA extracts are seen in this figure.

Thin layer chromatographic scanner analysis carried out at Southwestern Medical Center at Dallas showed that the average triptolide content of the Chinese EA extract from different batches manufactured by Huang Shi Pharmaceutical Company was 1.33 μg per mg[44,45]. The TEA extract produced by the present inventors contained much lower concentrations of triptolide of about 0.22 μg of triptolide per mg of extract. Analysis by TLC and HPLC indicated that the Chinese and Texas EA extracts contained some similar components (FIG. 23).

Comparative Studies

Comparison of the diterpenes in the ethyl acetate extracts of *Tripterygium wilfordii* Hook F prepared in China (CEA) and Texas (TEA) was performed. 330 mg of the TEA extract and 40 mg of the CEA extract were dissolved in ethyl acetate at a concentration of 66 mg/ml and 8 mg/ml, respectively, followed by sonication for 25 minutes and filtration in vacuum. The ethyl acetate solution was passed through a 5 g neutral $Al_2O_3$ column. The material was eluted with 30 ml of ethanol. After the ethanol elution was pooled with the ethyl acetate solution, the mixed solution was evaporated under nitrogen air till dryness. The residues were dissolved in 1 ml and 0.4 ml of chloroform, separately. 20 μl of each solution were applied to 20×20 cm silica gel G F 254 plate (polyester backing, 250 μm layer) and resolved with chloroform followed by chloroform/ether (1:4). Triptolide (3.6 μg), triptophenolide (10 μg) and tripdiolide (1.8 μg) served as reference standards. After the plates were air-dried, the diterpenes were visualized by the Kedde reaction. The relative concentrations of triptophenolide, triptolide and tripdiolide in the CEA, TEA and a standard extract were performed. The results of this study are shown in FIG. 25.

*TEA: the ethyl acetate extract of *Tripterygium wilfordii* Hook F prepared at UT Southwestern Medical Center at Dallas.

**CEA: the ethyl acetate extract of *Tripterygium wilfordii* Hook F prepared in China.

As shown in FIG. 23, the TEA extract evidenced a more heavy staining band for triptophenolide than did CEA, yet about equal to that of the standard. In contrast, the band for triptolide was more intense for CEA as compared to the TEA extract. These findings demonstrate that there is more triptolide in CEA (because it is made from unskinned roots). Therefore CEA is more toxic.

Stability

TEA is stable at room temperature for at least 1 year. Photosensitivity of TEA is unclear, and therefore, TEA is stored in the dark. It is expected that the preparation will remain stable for at least 8 years.

EXAMPLE 6

In Cellulo Activity of Tea Extract

Initial attempts to understand the mechanism of the action of TEA focused on its potential immunosuppressive activities. The present example demonstrates the significant in cellulo activity of the TEA extract on antigen and mitogen-induced T cell proliferation and IL-2 production.

The TEA extract was prepared as outlined in Example 5. TEA exerted a number of immunosuppressive effects on human immune responsiveness, including antigen and mitogen-induced T cell proliferation and IL-2 production. In cellulo (i.e., studies using intact whole cells) studies were carried out to determine the concentration of the TEA extract that inhibited mitogen or antigen induced human T cell proliferation and IL-2 production by T cells by 50% ($ID_{50}$).

Materials and Methods

Proliferation Studies:

T cells were cultured with or without PHA (0.5 µg/ml) in the presence or absence of TEA doses of 5.7 µg/ml, 7.3 µg/ml, 0.08 µg/ml, 1.32 µg/ml, 0.7 µg/ml and 1.0 µg/ml for 3 days. Significant effects on T cell proliferation were observed.

IL-2 Production Studies:

The effects of TEA on IL-2 production was examined. T cells were cultured with or without PHA (1 µg/ml) in the presence or absence of TEA at doses of 3.6 µg/ml, 3.9 µg/ml and 0.83 µg/ml. Significant effects on IL-2 production in the presence of either PHA or T.T. were observed (see Table 16).

The TEA extract at concentrations of 0.08–5.7 µg/ml inhibited proliferation and IL-2 production by about 50%. The concentrations of the TEA extract that induced death of about 50% of cells was also determined ($LD_{50}$). The $LD_{50}$ of the TEA extract on the mitogen or antigen activated T cells ranged from 17–70.5 µg/ml, which was 10–225 times the corresponding $ID_{50}$ (Table 16). These results demonstrate that the TEA extract retained strong potency for immunosuppressive activities in cellulo.

Much larger amounts of the TEA extract may be used with a significantly reduced toxicity level. Therefore, the ethyl acetate extract would be expected to be relatively safer than the $T_2$ extract.

TABLE 16

IN CELLULO $ID_{50}$ AND $LD_{50}$ OF TEA EXTRACT ON HUMAN PBMCS

| Assay | Stimulus | Length of Culture | $ID_{50}$ (µg/ml) | $LD_{50}$ (mg/ per ml) |
|---|---|---|---|---|
| Proliferation | | | | |
| | PHA (1 µg/ml) | 2.5 days | 5.7 | 70.5 |
| | PHA (1 µg/ml) + IL-2 (25 u/ml) | 2.5 days | 7.3 | 74.2 |
| | T.T (10 µg/ml) | 5 days | 0.08 | 18.8 |
| | T.T (10 µg/ml) + IL-2 (25 u/ml) | 5 days | 1.32 | 17.0 |
| | SK (1 mg/ml) | 5 days | 0.7 | 20.0 |
| | SK + (1 mg/ml) + IL-2 (25 u/ml) | 5 days | 1.0 | 19.8 |
| IL-2 production | | | | |
| | PHA (1 µg/ml) | 24 hrs. | 3.6 | |
| | PHA (1 µg/ml) | 24 hrs. | 3.9 | |
| | T.T. (10 µg/ml) | 24 hrs. | 0.83 | |

PHA, phytohemagglutinin; TT, tetanus toxoid; SK, streptokinase.

EXAMPLE 7

In Vivo Animal Studies of the Efficacy of Ethyl Acetate Extract of TWF

The present example describes studies that were conducted to demonstrate that the TEA extract of *T. wilfordii* exerts an immunosuppressive action on primary antibody responses in vivo.

In these studies, mice (C57 BL/6J) were immunized with TNP-BSA emulsified with complete Freund's adjuvant, according to techniques well known to those of skill in the art. The TEA extract was prepared as outlined in Example 5. On the day of immunization, the mice were begun on treatment with the TEA extract at 125 or 250 mg/kg/day orally. In other studies, mice were immunized with phosphorylcholine-KLH emulsified with complete Freund's adjuvant 30 days after the beginning of treatment with the TEA extract. Sera were harvested 10 and 26 days after immunization. Antibodies against TNP, TNP-BSA or PC-KLH in these sera were determined by the ELISA method. The ELISA method is a standard immunoreactivity assay well known to those of skill in the art.

Results from these studies show that the primary antibody responses to each of these antigens were markedly decreased in the mice treated with the TEA extract (Table 17). Treatment beginning 30 days before immunization was the most effective at suppressing antibody responses, but treatment beginning on the day of immunization also significantly diminished antibody responses.

TABLE 17

EFFECT OF TREATMENT OF MICE WITH THE TEA EXTRACT ON
THEIR CAPACITY TO GENERATE PRIMARY ANTIBODY RESPONSES

| | | Treatment with TEA Extract | | | | |
|---|---|---|---|---|---|---|
| | | Daily dose (mg/kg of body weight) | before immunization (days) | after immunization (days) | Antibody | |
| Antigen Immunization | Assay | | | | Serum Dilution | OD |
| PC-KLH | PC-KLH | 0 | 30 | 10 | 1:80 | .250 |
| | | 125 | 30 | 10 | | .133 |
| | | 250 | 30 | 10 | | .084 |
| TNP-BSA | TNP-BSA | 0 | 0 | 10 | 1:320 | .671 |
| | | 125 | 0 | 10 | | .373 |
| | | 250 | 0 | 10 | | .454 |
| | | 0 | 0 | 26 | 1:5120 | .528 |
| | | 125 | 0 | 26 | | .364 |
| | | 250 | 0 | 26 | | .282 |
| TNP-KLH | TNP | 0 | 0 | 10 | 1:20 | .414 |
| | | 125 | 0 | 10 | | .375 |
| | | 250 | 0 | 10 | | .768 |
| | | 0 | 0 | 26 | 1:320 | .639 |
| | | 125 | 0 | 26 | | .552 |
| | | 250 | 0 | 26 | | .280 |

C57 BL/6J mice (5 in each group) were treated without or with varying doses of the TEA extract orally. 100 mg of the antigens emulsified in 0.1 ml of complete Freund's adjuvant were injected intraperitoneally on the same day as the EA treatment started or 30 days after the beginning of treatment with the TEA extract. Blood was taken from the tail vein on the 10th or 26th day after immunization. Antibodies against TNP alone or TNP-BSA or PC-KLH in the sera were determined with ELISA. Relative amount of antibodies in the sera was estimated by comparing the O.D. readings of each sample at the same dilution for individual assays. Multiple dilutions of serum were assayed and data shown for the dilutions at which all readings were on the linear part of the curve.

EXAMPLE 8

Toxicity of Tea Extracts

The present example is provided to demonstrate the reduced toxicity of the TWF preparations, particularly the TEA abstract of the present invention as compared to other T. wilfordii extracts.

Acute toxicity testing was carried out using C57 BL/6J mice. For the initial studies, 25 mice (5 in each group) were used to estimate the approximate $LD_{50}$. No deaths developed with the ethyl acetate preparation of T. wilfordii until very high doses of 1200 mg/kg were administered. Eighty percent of the mice treated with 1400 mg/kg of the TEA extract died. Following this, 50 mice of the same strain were divided into 5 groups with equal numbers of each sex in each group. Mice were given a single dose of the TEA extract orally at 0, 1100, 1150, 1230, 1350 and 1500 mg/kg body weight. The mice were observed for 7 days thereafter. The $LD_{50}$ was estimated according to the Spearman-Karber Method[62]. $LD_{50}$ of the TEA extract from this experiment was 1253 mg/kg/day (Table 19). All death occurred within the first 3 days of the study.

TABLE 18

ACUTE TOXICITY TEST OF THE TEA EXTRACT IN MICE

| Dose (mg/kg) | Xi | Ri | Ni | Pi | $\frac{Pi + Pi + 1}{2}$ | I |
|---|---|---|---|---|---|---|
| 1100 | 3.04 | 0 | 10 | 0 | 0.15 | 0.02 |
| 1150 | 3.06 | 3 | 10 | 0.3 | 0.35 | 0.03 |
| 1230 | 3.09 | 4 | 10 | 0.4 | 0.55 | 0.04 |
| 1350 | 3.13 | 7 | 10 | 0.7 | 0.85 | 0.05 |
| 1500 | 3.18 | 10 | 10 | 1.0 | | |

50 mice (C57BL/6j) were randomly divided into 5 groups with equal number sof each sex for each group. The mice were treated with various doses of the TEA extract as indicated orally for 7 days. The number of dying mice was recorded. $LD_{50}$ was calculated according to Spearman - Karber method:
If $X = LD_{50}$,
Log $X = X_k - \Sigma [(Pi + Pi +_1) \times I \times 0.5]$.
Log $X = 3.098$
$LD_{50} = 1253.1$ mg/Kg.
$Xi = Log_{dose}$; $Ri$ = number of dying mice; $Ni$ = number of tested mice; $Pi$ = (Ri/Ni); $I = Xi+_1 -Xi$; $X_k$ = the logarithm of the dose (k) at which all treated animals died.

Autopsy was performed immediately after death of the mice. Histological examination demonstrated marked lymphocytic necrosis of splenic germinal centers and thymus, with only mild changes in liver, kidney, lung or brain of some of the animals.

TABLE 19

COMPARISON OF THE TEA WITH THE CEA EXTRACT

| | EA Extract | |
|---|---|---|
| | TEA | CEA |
| Source of plant material | Fujian province | Hubei province |
| Portion of the plant the | woody portion of | whole roots |

TABLE 19-continued

COMPARISON OF THE TEA WITH THE CEA EXTRACT

|  | EA Extract | |
| --- | --- | --- |
|  | TEA | CEA |
| EA extracted from | the roots | |
| Triptolide content | | |
| (µg/gm of plant material) | 4.80 | 27.50 |
| (µg/mg of the EA extract) | 0.22 | 1.33 |
| $ID_{50}$ (in vitro on PHA stimulated human T cell proliferation, µg/ml) | 5.7 | 2.0 |
| $LD_{50}$ (on mice, mg/kg of body weight) | 1253 | 764* |
| $ID_{50}$ in vitro T-cell proliferation/$LD_{50}$ ratio (on mice) | $4.5 \times 10^{-1}$ | $2.6 \times 10^{-3}$ |

*The average of the $LD_{50}$ of different batches of tablets of the CEA extract prepared from TWH obtained from different counties or provinces of China.

As shown in Table 19, the $LD_{50}$ dose of the Chinese preparation is about 764 mg/kg as compared to 1253 mg/kg for the TEA extract. The $LD_{50}$ of $T_2$ in mice has been reported to be 159.7 ± 14.3 mg/kg 40 and the $LD_{50}$ of the CEA extract varied from 608–858 mg/kg. The $ID_{50}$ of the Chinese preparation (CEA) is 2.0 µg/ml as compared to 5.7 for the TEA extract. The $ID_{50}/LD_{50}$ ratio of the CEA extract is $2.6 \times 10^{-3}$. This therapeutic activity:toxic index value is significantly lower than the $ID_{50}/LD_{50}$ ratio of the TEA extract, $ID_{50}:LD_{50}=4.5 \times 10^{-3}$. The ratios of each of the extracts as calculated with the data presented in Table 19 indicate that the TEA extract has a superior therapeutic activity:toxic index balance, and thus is superior as a therapeutic preparation compared to preparations of TWHF described in the literature.

EXAMPLE 9

In Vivo Use of Tea Extract

The present example is provided to outline the use of the TEA preparations in animals, particularly humans.

The dosage schedule of the TEA extract to be used in initial escalation and safety studies will be calculated using the $LD_{50}$ of the TEA extract and its triptolide content. The TEA extract was processed using the same procedure as used in China to produce the CEA extract with the exception that the material prepared as the TEA (Texas ethyl acetate extract) is extracted from the peeled woody portion of the roots of TWH. The CEA extract is extracted from the whole root of the plant. The reported dosage of the CEA extract will be employed as a reference for calculating the dosage of the TEA extract (Table 19). The Chinese literature reports that 60–120 mg/day of the CEA extract is safe and effective in the treatment of RA (Shu et al., 1989; Hubei cooperative study group, 1981). This amount of the CEA extract contains 131.2–262.4 µg of triptolide per tablet. Clinical trials with the TEA extract will employ escalating doses of 30 mg, 60 mg and 120 mg/day in three divided doses. The lowest dose is equivalent to approximately 25% of the smaller dosage of the CEA extract used safely in China whereas the highest dosage (120 mg dose of the TEA extract) approximates the lowest dosage of the CEA extract used in China and contains 26.4 µg of triptolide.

Administration of extracts of TWH are contraindicated in patients with leukopenia, thrombocytopenia, and impaired liver or kidney function. Studies have not been done to assess the effects of $T_2$ on pregnant or lactating women.

Patients will discontinue treatment with extracts of TWH if they develop any of the following: persistent vomiting or diarrhea; profound anorexia; WBC count of $\leq$ 2,500 cells/mm$^3$, or platelet count of $\leq$ 100,000 cells. Patients who develop these symptoms should be monitored frequently for white blood cell counts, as well as liver and kidney function.

EXAMPLE 10

Fraction 924 of TWF-characterization and Identification

The present example is provided to detail the biological activity of a fraction 924 component of a *T. wilfordii* ethyl acetate extract.

Based on previous examples, the present inventors were aware that many diterpenoid compounds of TWHF, such as triptolide, possess suppressive capacity on both in vitro and in vivo immune functions. The radical groups responsible for the immune suppressive function of these compounds are unknown, however, the core structure of diterpenoids which may be related to their activity consists of an α-β-unsaturated 5 element lactone which can be identified by Kedde agents. HPLC was used to fractionate the ethyl acetate extract of TWHF (TEA) and the Kedde reagents were employed to trace the fractions. Then, the effect of selected fractions on the in vitro IL-2 production and [$^3$H]-thymidine incorporation by PHA-activated T cells was determined. The most active fraction to inhibit these T cell functions was selected and its chromatographic pattern was identified with HPLC. The fraction was further purified with HPLC and crystallized repeatedly; a pure, crystallized compound was obtained and designated "924".

Purification of a 924 Fraction from an Ethyl Acetate Extract

The dried woody skinned part of the root of TWHF was extracted with ethanol. The solution was concentrated at reduced pressure, and the residue was dissolved in ethyl acetate. This solution was passed through $Al_2O_3$ with ethanol as an eluent. The eluate was evaporated and the residue chromatographed on silica gel with chloroform, chloroform-ether and ethyl acetate as successive eluent. The fractions eluted with chloroform-ether were purified on a preparative HPLC column packed with Nova-Pak C18 and equipped with a 214 detector. Methanol-water was the mobile phase. A fraction having positive reaction to Kedde reagent was collected and extracted with chloroform. The chloroform solution was evaporated to dryness and the residue crystallized in dichloromethene-hexane to yield 924. "924" is soluble in ethanol, and ethanol and chloroform.

The "924" fraction inhibited DNA synthesis by T cells stimulated with PHA. The "924" fraction at a concentration of 1 ng/ml or more inhibited PHA-stimulated T cells to uptake [$^3$H]-thymidine. The inhibition capacity was correlated with the concentrations of the compound. The slope of the inhibition curve of "924" on T cell proliferation was quite flat that the inhibition rate changed from 14.6% to 54.2% when the concentration of "924" increased from 1 ng/ml to 100 ng/ml. This was different from some components of TWHF, such as triptolide or tripdiolide which exerted potent immunosuppressive action with increase in its concentrations at the level of ngs, and resulted in significant enhancement of the inhibition of the cell function.

Figure 22A:
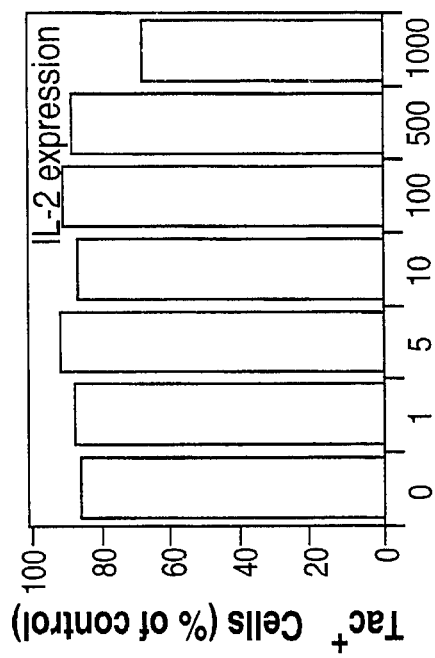
FIGS. 22A–22D show the function of Fraction 924; 22A shows the effect of Fraction 924 on IL-2 production; 22B, the effect on IL-2 expression; 22C, the effect on T-cell proliferation; and 22D, the effect on cell viability.
Figure 22B:
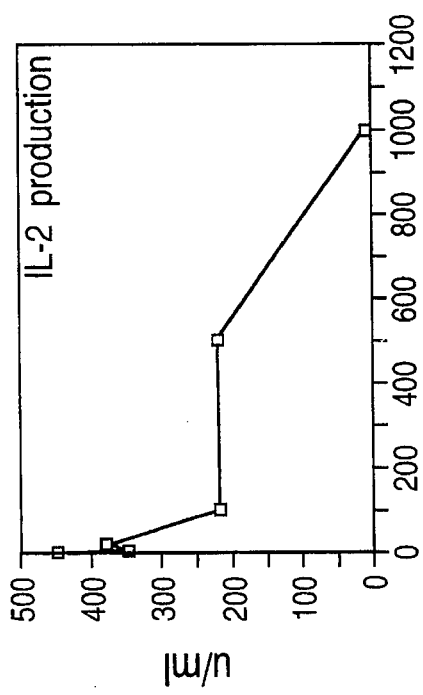

The "924" fraction inhibited IL-2 production by PHA-stimulated T cells. Similar with the pattern of the inhibitory effect of "924" on T cell DNA synthesis, at the inhibitory concentrations, "924" was able to reduce the production of IL-2 by PHA-induced T cells. A 50% reduction of IL-2 secretion was seen at 42.11 ng/ml (see FIG. 22B).

Figure 22C:
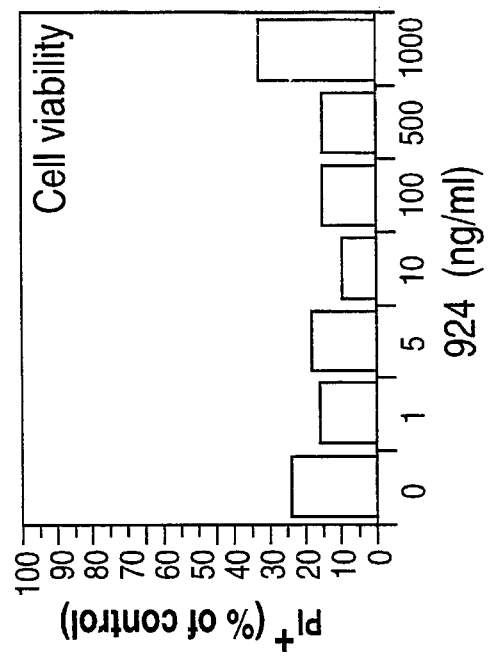

The 924 fraction also demonstrated significant activity in inhibiting proliferation of T cells, providing for inhibition of T cell proliferation at relatively low doses of 200 ng/ml of fraction 924 (see FIG. 22C). At concentrations of 1,000 ng/ml fraction 924, no cell proliferation was evident (see FIG. 22C). There was no effect of "924" on IL-2R expression by PHA-activated T cells. Fraction "924" at 500 ng/ml (at least 50 times the concentration effective to inhibit T cell proliferation or IL-2 production) did not affect the IL-2R expression by PHA-activated T cells.

Figure 22D:
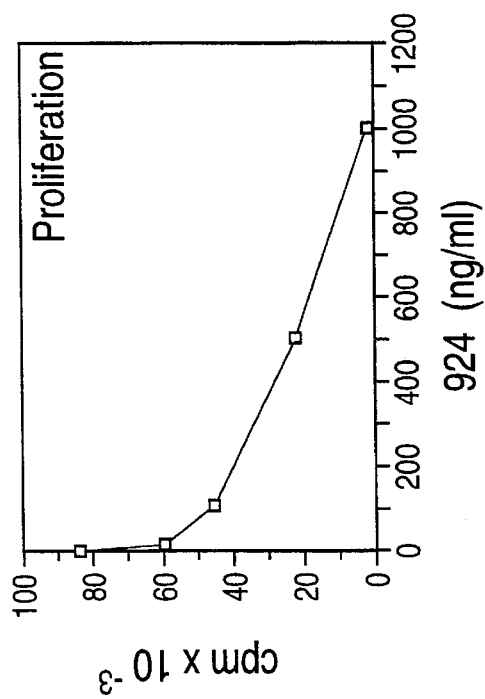

Fraction "924" did not affect the viability of PHA-stimulated T cells at all employed concentrations, ranging from 1 ng/ml up to 1000 ng/ml. The in vitro ID50/LD50 of "924" of T cell proliferation was more than 10 indicating that, under the same cultural conditions, "924" did not increase cell death until it reached to 10 times more than its inhibitory concentration. The 924 fraction also demonstrated relatively low cell toxicity, as demonstrated in FIG. 22D. Concentrations of the 924 fraction of between 1 and 500 ng/ml did not differ significantly in terms of cell viability, expressed as a percent of viable cells in the control population. A 924 fraction concentration of 1,000 ng/ml was only slightly more toxic to cell viability as compared to the 0 ng/ml dose (see FIG. 22D, 0 ng/ml=22% of control; 1,000 ng/ml fraction 924=35% of control cell viability).

Figure 20:
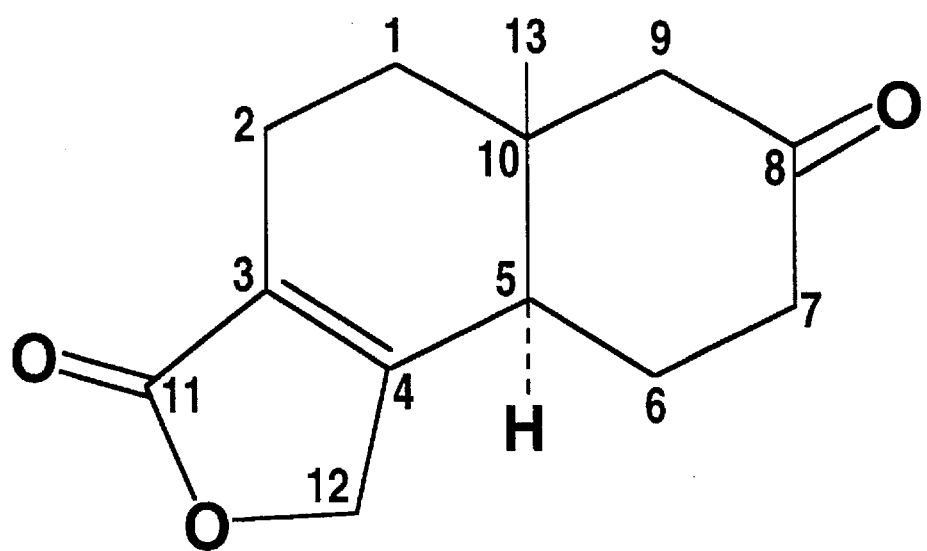
FIG. 20 depicts the structure of wilforonide (Naphtho-[1,2-c] furan-3,7(1H,5H)-dione, 4,5a,6,8,9,9a-hexahydro-5a-methyl-(5aR-trans)-[104331-87-5]).
Figure 21A:
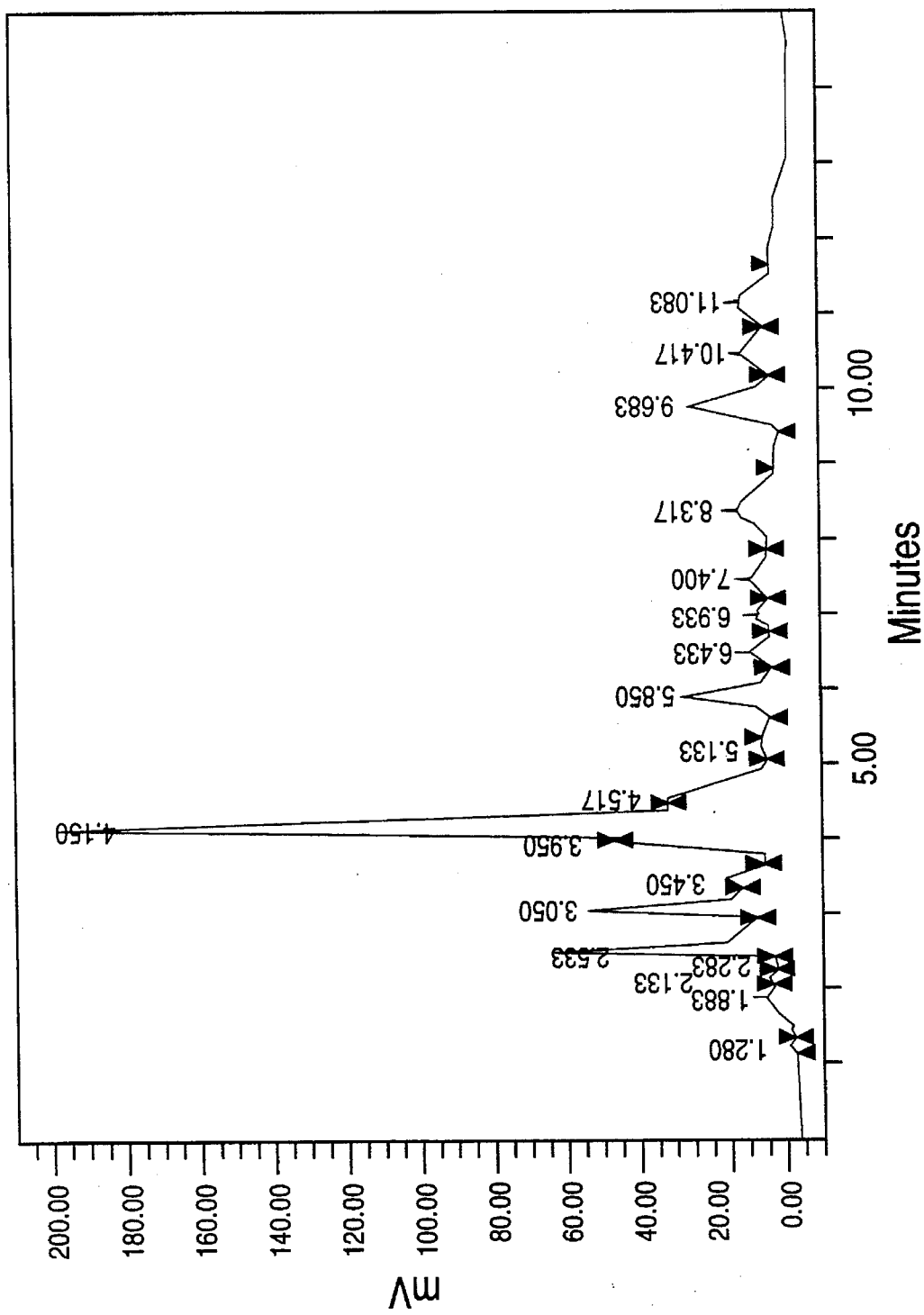
FIGS. 21A and 21B show the elution profile of Fraction 924.
Figure 21B:
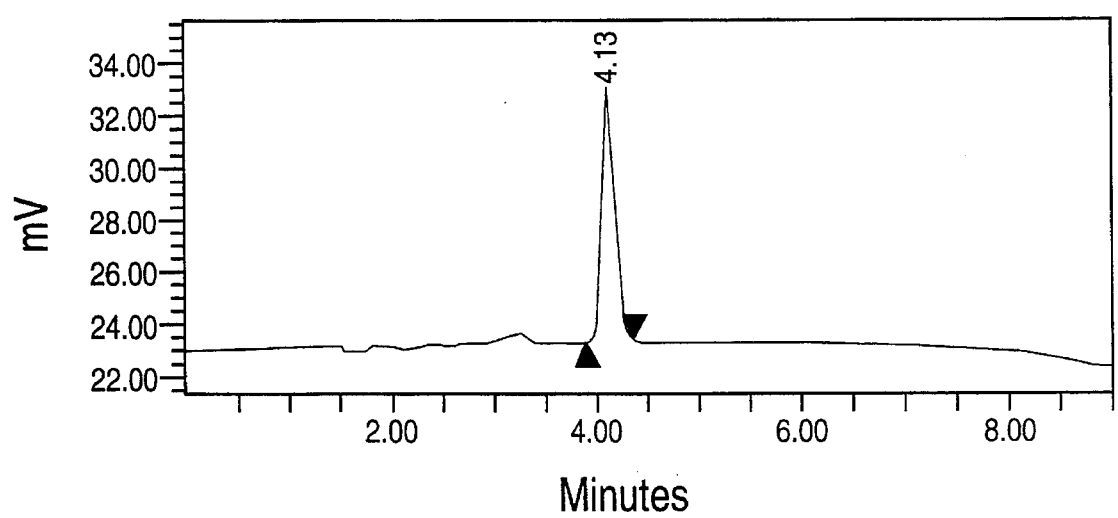

The positive reaction to Kedde reagent indicated that the "924" has a structure of an $\alpha,\beta$-unsaturated lactone. Since many of the known diterpenoid compounds such as triptolide, triptochlorolide, 16-hydroxytriptolide, tripdiolide, triptonide and triptophenolide also have the $\alpha,\beta$-unsaturated lactone, the TLC and HPLC patterns of "924" were compared with these compounds. The pattern of "924" was different from that of all of the above mentioned compounds. The pattern did not have the chromatographic characteristics of diterpenoids and did not follow the regular pattern of diterpenoids tested by several normal and reverse phase chromatographic systems. Therefore, "924" seems to be a non-diterpenoid compound. Upon further analysis of the 924 fraction by NMR/mass spectroscopy, the fraction was determined to be the pure compound, wilforonide (FIG. 20).

EXAMPLE 11

Immunosuppressive Effects of Wilforonide

T cells were cultured with or without PHA(0.5 micrograms/ml) in the presence or absence of either, 10 ng/ml, 50 ng/ml, 100 ng/ml, 200 ng/ml or 500 ng/ml concentrations of the wilforonide preparation described in Example 10 for three days. [$^3$H]-thymidine was added for the last 14 hours of culture. Each concentration was run in quadruplicate (4 times) and the results for each concentration averaged to provide a mean. The mean cpm $\times 10^3$ values were combined and expressed as a percent of T cell inhibition. These data are provided at Table 20.

As shown in Table 20, a concentration of 100 ng/ml wilforonide provided a 21.19% inhibition of PHA-induced T cell proliferation in cellulo. A concentration of 200 ng/ml wilforonide provided a 26.43% inhibition of PHA-induced T cell proliferation. A concentration of 500 ng/ml wilforonide resulted in a 62.86% inhibition of PHA-induced T cell proliferation (see Table 20). An $ID_{50}$ of 391.30 ng/ml wilforonide was observed (see Table 20).

TABLE 20

EFFECT OF WILFORONIDE ON PHA-INDUCED T CELL PROLIFERATION*

| Wilforonide | cpm $\times 10^3$ | | | | Mean | % |
|---|---|---|---|---|---|---|
| (ng/ml) | 1. | 2. | 3. | 4. | cpm $\times 10^3$ | inhibition |
| 0 | 34.1 | 36.9 | 58.5 | 38.5 | 42.0 | |
| 10 | 23.5 | 37.1 | 57.5 | 36.3 | 38.6 | 8.09 |
| 50 | 30.2 | 35.3 | 57.0 | 44.8 | 41.8 | 0.48 |
| 100 | 13.0 | 37.6 | 55.2 | 26.7 | 33.1 | 21.19 |
| 200 | 6.8 | 33.9 | 56.5 | 26.4 | 30.9 | 26.43 |
| 500 | 0.3 | 19.7 | 30.9 | 11.3 | 15.6 | 62.86 |
| $ID_{50}$ (ng/ml) | | | | | | 391.30 |

*T cells were cultured with or without PHA (0.5 μg/ml) in the presence or absence of the indicated concentrations of wilforonide for 3 days. [$^3$H]-Thymidine was added for the last 14 hours. Data are from 4 independent experiments.

Effect of Wilforonide on PHA-induced IL-2 Production

The effects of wilforonide on IL-2 production was also examined. T cells were cultured with or without PHA(1 microgram/ml) in the presence or absence of 0 (control), 10 ng/ml, 50 ng/ml, 100 ng/ml or 200 ng/ml wilforonide overnight. Cell-free supernants were diluted 1 to 80 IL-2 content assay with CTLL-2 cells. IL-2 production by the T cells cultured without stimulation was found to be less than 0.32 units/ml.

The results obtained from the study are provided in Table 21. The 10 ng/ml concentration of wilforonide evidenced a 37.94% inhibition of PHA-induced IL-2 production relative to control. The 50 ng/ml concentration of wilforonide resulted in a 54.22% inhibition of PHA-induced IL-2 production relative to control. Concentrations of 100 NG/ML resulted in a 68.20% inhibition, with the 200 ng/ml wilforonide concentration resulting in a 74.96% inhibition of PHA-induced IL-2 production.

An overall $ID_{50}$ of 42.11 ng/ml was also determined. These data are provided in Table 21.

TABLE 21

EFFECT OF WILFORONIDE ON PHA-INDUCED IL-2 PRODUCTION*

| Wilforonide | IL-2 (unit/ml) | | | | | % |
|---|---|---|---|---|---|---|
| (ng/ml) | 1. | 2. | 3. | 4. | Mean | Inhibition |
| 0 | 1.422 | 23.436 | 50.020 | 10.701 | 21.395 | |
| 10 | 1.628 | 20.723 | 27.374 | 3.385 | 13.278 | 37.94 |
| 50 | 1.664 | 26.983 | 4.509 | 6.042 | 9.795 | 54.22 |
| 100 | 0.800 | 11.160 | 10.170 | 4.982 | 6.803 | 68.20 |
| 200 | 0.850 | 10.301 | 8.502 | 1.773 | 5.357 | 74.96 |
| $ID_{50}$ (ng/ml) | | | | | | 42.11 |

*T cells were cultured with or without PHA (1 μg/ml) in the presence or absence of the indicated concentrations of wilforonide overnight. Cell-free supernatants were diluted I to 80 for IL-2 content assay with CTLL-2 cells. IL-2 production by the T cells cultured without stimulation was less than 0.32 unit/ml.

Inhibitory Effect of Wilforonide on Antigen-induced T Cell Proliferation

T cells were cultured with or without SK (1 ng/ml) or SK+IL-2 (50 u/ml) or SK+PMA (0.2 ng/ml) in the presence or absence of the following concentrations of wilforonide:

10 ng/ml, 50 ng/ml, 100 ng/ml, 500 ng/ml or 1,000 ng/ml. The cells were allowed to culture for five days. The cultures were pulsed with [$^3$H]-thymidine for the last 24 hours of culture. The data collected from this study is provided in Table 22. These data represent the mean of the percent inhibition of [$^3$H]-thymidine incorporation of five independent experiments. ID$_{50}$ were calculated based on the regression formula by using the fx-3600 calculator. T cells cultured with SK or SK+IL-2 or SK+PMA gave cpm of $1.87 \times 10^3$, $4.99 \times 10^3$ and $6.67 \times 10^3$, respectively.

The response to SK inhibited by low concentrations Wilforonide is shown to be partially overcome by adding IL2 or PMA, as demonstrated by the markedly higher (increased) ID$_{50}$. This indicates that inhibition correlates to a decrease in IL2 production. This decrease is overcome by adding IL2 or co-stimulating with PMA that induces IL-2 production.

The data from this study is provided in Table 22.

TABLE 22

INHIBITORY EFFECT OF WILFORONIDE
ON ANTIGEN-INDUCED T CELL PROLIFERATION*

| Wilforonide (ng/ml) | SK | SK + IL-2 | SK + PMA |
|---|---|---|---|
| 10 | 42.15 | 19.59 | 22.67 |
| 50 | 44.47 | 12.37 | 17.70 |
| 100 | 49.14 | 14.52 | 20.32 |
| 500 | 75.20 | 61.70 | 53.30 |
| 1,000 | 84.23 | 86.21 | 65.43 |
| ID$_{50}$ (ng/ml) | 127.12 | 476.00 | 613.00 |

*T cells were cultured with or without SK (1 mg/ml) or SK plus IL-2 (50 u/ml) or SK plus PMA(.2 ng/ml) in the presence or absence of indicated concentrations of wilforonide for 5 days. Cultures were pulsed with [$^3$H]-thymidine for the last 24 hours. Data represent the mean of the % inhibition of [$^3$H]-thymidine incorporation of 5 independent experiments. ID$_{50}$ were calculated based on the regression formula by using the fx-3600 calculator. T cells cultured with SK or SK + IL-2 or SK + PMA gave cpm of $1.87 \times 10^3$, $4.99 \times 10^3$ and $6.67 \times 10^3$, respectively.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutions and modifications apparent to those skilled in the art or deemed to be within the spirit, scope and concept of the invention as defined by the appended claims. All claimed matter and methods can be made and executed without undue experimentation.

REFERENCES

The following references, to the extent that they provide exemplary procedural or other details supplementary to those set forth herein, are specifically incorporated herein by reference.

1. Kirkman et al. (1989) "Response to monoclonal CD7 antibody in rheumatoid arthritis" *Lancet* 1:589.

2. Caperton et al. (1989) "Treatment of refractory rheumatoid arthritis (RA) with anti-lymphocyte immunotoxin" *Arthritis Rheum.* 24:2130.

3. Herog et al. (1989) "Anti-CD4 antibody treatment of patients with rheumatoid arthritis: I. Effect on clinical course and circulating T cells" *J. Autoimmunity* 2:627.

4. Kyle et al. (1989) "Beneficial effect of monoclonal antibody to interleukin 2 receptor on activated T cells in Rheumatoid arthritis" *Ann. Rheum. Dis.* 48:428.

5. Jia Li (1985) "Chemistry and pharmacology and clinical application of plants of Tripterygium family" *Yao Xue Tong Bao* 20:101.

6. Hubei Study Group (1982) "Pharmacological study on the ethanol extract of *Tripterygium wilfordii* Hook F" *Zung Cao Yao* 13:27.

7. Wei et al. (1988) "Side effects of T$_2$ in the treatment of 106 patients with glomerular diseases" *New Drug and It's Clinical Application* 1(6):37.

8. Jiang et al. (1987) "*Tripterygium wilfordii* Hook caused acute toxicity with kidney involvement in 17 cases" *Chinese J. Kidney Dis* 3(3):167.

9. Chen et al. (1987) Clinical analysis of 10 cases of *Tripterygium wilfordii* Hook caused toxicity" Symposium, "Clinical Application of *Tripterygium wilfordii* Hook", Hubei, China.

10. Tao et al. (1987) "Prospective, controlled, double-blind, cross-over trial of T$_2$ (polyglycosides extracted from *Tripterygium wilfordii* Hook F) in the treatment of rheumatoid arthritis" *Chinese J. Int. Med.* 26:399.

11. Tao et al. (1988) "Mechanism of treatment of rheumatoid arthritis with *Tripterygium wilfordii* Hook F I. Effect of T$_2$ on secretion of total IgM and IgM-RF by PBMC" *Acta. Acad. Med. Sinicae* 10:361.

12. Tao et al. (1989) "A prospective, controlled, double blind, cross-over study of *Tripterygium wilfordii* Hook F in the treatment of rheumatoid arthritis" *Chinese Med. J.* 102(5):327.

13. (1982) "T$_2$ Study Group of Jiang Su Province of China: Summary of the clinical trials of T$_2$ in the treatment of 554 patients with various diseases." *Annals Chinese Acad. Med. Sci.* 3:3.

14. Yu, Dy Y (1983) "Clinical observation of 144 cases of rheumatoid arthritis treated with glycoside of radix *Tripterygium wilfordii*" *J. Trad. Chinese Med.* 3(2):125.

15. Xue, Z (1984) "Treatment of 21 cases of systemic lupus erythematosus (SLE) with *Tripterygium wilfordii*" *Chinese J. Derm* 17(3):201.

16. (1979) "T$_2$ Study Group of Chinese Institute of Dermatology: Clinical observation on the treatment of skin disorders with polyglycoside of *Tripterygium wilfordii*" *Acta. Acad. Med. Sinicae* 1(2):6.

17. Xie, D (1983) "Experience in the treatment of Behcet's disease with polyglycosides of *Tripterygium wilfordii* Hook" *Zhong Xi Yi Jie HE ZA Zhi* 3(6):349.

18. Peng, S (1983) "Report on 20 patients with Henoch-Schonlein purpura treated with polyglycosides of *Tripterygium wilfordii* Hook (T$_2$)" *Jian Su Yi Yao* 11:38.

19. Feng, B (1985) "Observation on the effect of polyglycosides of *Tripterygium wilfordii* Hook (T$_2$) on 50 cases of leprosy reactive status" *Chinese Clin. Derm. J.* 4:211.

20. Wu, Y (1986) "Treatment of neuralgia of leprosy reactive status with polyglycosides of *Tripterygium wilfordii* Hook (T$_2$)" *Chinese J. Derm.* 19(4):217.

21. Jiang, X (1982) "Exploration of the treatment of nephrotic syndrome with polyglycosides of *Tripterygium wilfordii* Hook (T$_2$)" *Chinese J. Ped* 20(4):201.

22. Li, X (1982) "Clinical observation on the treatment of 53 cases of nephrotic syndrome with polyglycosides of *Tripterygium wilfordii* Hook (T$_2$)" *Chinese J. Ped.* 20(4):203.

23. Qian, J (1987) "Observation on the effect of polyglycosides of *Tripterygium wilfordii* Hook ($T_2$) on idiopathic IgA nephropathy" *Annual Meeting of Nephrology* (People's Republic of China).

24. Li, X (1987) "Treatment of 50 cases of children's purpura nephritis with polyglycosides of *Tripterygium wilfordii* Hook" *Jiang Su Yi Yao* 12:644.

25. Pan, Y (1987) "Treatment of purpura nephritis with *Tripterygium wilfordii* Hook" *Acta. Acad. Med. Sinicae* 9(6):2.

26. Cheng, R (1988) "Observation of the therapeutic effect of polyglycosides of *Tripterygium wilfordii* Hook ($T_2$) combined with thyroid gland tablets on chronic lymphocytic thyroiditis" *Zhong Xi Yi Jie He Za Zhi* 8(11):676.

27. Zheng et al. (1983) "Studies on toxicity of total glycosides in *Tripterygium wilfordii*" *Acta. Acad. Med. Sinicae* 5(2):73.

28. Zuo et al. (1986) "Different effect of *Tripterygium reglii* on T and B cell function" *Chinese J. Immunol.* 2:232.

29. Zhang, LS (1986) "Inhibitory effect of celastrol on murine lymphocyte proliferation" *Acta. Pharmacol. Sinicae* 7:85.

30. Zang et al. (1986) *Shanghai Yike Dalle Xueba*, 13(4):267–272.

31. Kupchan et al. (1972) *J. Am. Chem. Soc.*, 94:3194–3195.

32. Zheng et al. (1983) "Studies on pharmacological actions of total glycosides in *Tripterygium wilfordii* Hook F" *Acta. Acad. Med. Sinicae* 5:1.

33. Chang et al. (1984) "A preliminary study of the immunosuppressive activity of mixed glycosides of *Tripterygium wilfordii* Hook F" *Chinese J. Immunol.* 4:331.

34. Zheng et al. (1982) "Effect of the decoction of *Tripterygium wilfordii* Hook on immune functions" *Fujiang Med. J.* 4:222.

35. Zhang et al. (1983) "Studies on diterpenoids from *Tripterygium wilfordii*" *Acta. Acad. Med. Shanghai* 13:267.

36. Zhang et al. (1981) "Antineoplastic action of triptolide and its effect on the immunologic function in mice" *Acta. Pharmacol. Sinicae* 2(2):128.

37. Cheng HW et al. (1985) "Cellular immunological study on experimental allergic encephalopathy and the exploration of the effect of *Tripterygium wilfordii* Hook on it", *Immunology Bulletin* 5(3,4):7.

38. Zheng J et al. (1983), Studies on toxicity of total glycosides in *Tripterygium wilfordii*. Acta Acad Med Sinicae 5(2):73.

39. Zheng JR et al. (1985a), Effect of total glycosides of *Tripterygium wilfordii* on animal reproductive organs. 1. Experiments of male rats. Acta Academiae Sinicae 5(2):73.

40. Kupchan, SM (1976) "Novel plant-derived tumor inhibitors and their mechanisms of action" *Cancer Treatment Reports* 60:1115.

41. Hubei Cooperative Study Group of *Tripterygium wilfordii* Hook (1981), Clinical study of the extract of *tripterygium wilfordii* hook in the treatment of rheumatoid arthritis. Wu Han Yi Xue Yuan Xue Bao 4:62, 1981.

42. Chen, Zizhen, et al. (1986), Proceedings in the study of the active compounds of *Tripterygium wilfordii* Hook F. Zong Guo Yi Yaun Yao Xue Za Zhi. 6(9):26.

43. Chen, Zizhen, et al. (1988), Study of the active compounds and the preparation of *Tripterygium wilfordii*. Hook F. Zi Liao Hui Bian. 6–9.

44. Chen, Zizhen et al. (1985), Quantitative measurement of triptolide content in the tablets of *Tripterygium wilfordii* Hook F. Zi Liao Hui Bian.

45. Fang, Guoxin et al. (1986), Quantitative measurement of triptolide contained in the ethyl acetate extract of *Tripterygium wilfordii* Hook F and its tablets. Zhong Tao Tong Bao 11(8):38.

46. Zhang, Yigu et al. (1983) "An experimental pathological study of intoxication by the ethyl acetate extract of Lei Gung Teng (*Tripterygium wilfordii* Hook F)", *Yao Wu Yan Jiu* 4:367.

47. Li, Lezhen et al. (1982), Pharmacological study of the ethyl acetate extract of *Tripterygium wilfordii* Hook F. Zhong Cao Yao 13(4):27.

48. Hubei Cooperative Study Group of *Tripterygium wilfordii* Hook F (1979), Preliminary pharmacologic study of *Tripterygium wilfordii* Hook F. Hubei Wei Sheng 1:73.

49. Phytochemistry Study Group of Hubei Academy of Chinese Traditional Medicine and Therapy. Study of the active ingredients of *Tripterygium wilfordii* Hook F in the treatment of rheumatoid arthritis (1978), Zhong Cao Yao Tong Xum. 11:8.

50. Chen Kunchang et al. (1986), "The lactores from three wingnut (*Tripterygium wilfordii* Hook F) in Huber", *Chem. Abstracts*, Vol. 105:384, abstract No. 105:130886u.

51. Thiele et al. (1983), *J. Immunol.* 131:2282–2290.

52. Rosenberg, et al. (1979), *J. Immunol.* 122:926–931.

53. Rosenstreich, et al. (1971), *J. Exp. Med.* 134:1170–1186.

54. Jelinek et al. (1986), *J. Immunol.* 136:83–92.

55. Geppert et al. (1987), *J Immunol.* 138:1660–1666.

56. Davis et al. (1986), *J Immunol.* 137:3758–3767.

57. Moreno et al. (1986), *J Immunol.* 136:3579–3587.

58. Gillis et al. (1978), *J Immunol.* 120:2027–2032.

59. Splawski et al. (1986), *J Immunol.* 139:1432–1437.

60. Weiss et al. (1986) "The role of the T3/antigen receptor complex in T cell activation" *Ann. Rev. Immunol.* 4:593.

61. Remington's Pharmaceutical Sciences (1990), 18th edition.

62. Delaunois, A.L. (1973), International encyclopedia of Pharmacology and Therapeutics, Section 7, *Biostatistics in Pharmacology*, Vol. II, Pergamon Press.

63. Zalkow et al. (1988) "Macrocyclic pyrolizidine alkaloids from Senecio anonymous. Separation of a complex alkaloid extract using droplet countercurrent chromatography" *J. Nat. Prod.* 31:1520.

64. Shu, Dafeu et al. (1989), Report of 270 cases of rheumatoid arthritis treated with ethyl acetate extract of *Tripterygium wilfordii* Hook. Zhong Yao Yao Li Yu Lin Chuang, 5(3):40.

65. Zhang LS (1986), Inhibitory effect of celastrol on murine lymphocyte proliferation. Acta Phamacol Sinicae 7:85.

66. Nan Jiang Jun Ou Zong Yi Yuan (1979), Effect of T II and Huang Jiang (Po) on lymphocytes. Zi Liao Xuan Bian 10:5.

67. Kuang Yan De et al. (1988), Effect of TWH on IL-2 production and IL-2 receptor expression. Shanghai J Immunology 8(4):250.

68. Zhu Xi Yuan et al. (1988), In vitro observation on the effect of *Tripterygium hypoglaucum* hutch on immune responses. Physiological Sciences 8:417.

69. Zheng YL et al. (1982) "Effect of the decoction of *Tripterygium wilfordii* Hook on immune functions", *Fujiang Med J.* 4:222.

70. Chang JL et al. (1984) "A preliminary study of the immunosuppressive activity of mixed glycosides of *Tripterygium wilfordii* Hook F." *Chinese J. Immunol.* 4:331.

71. Zheng JR et al. (1985b), Effects of total glycosides of *Tripterygium wilfordii* on reproductive organs of experimental animals. II. Experiments in female rats. Acta Academiae Sinicae 7(4):256.

What is claimed is:

1. A *Tripterygium wilfordii* Hook F preparation, obtained from the woody portion of the *Tripterygium wilfordii* Hook F root, having a triptolide concentration of about 0.2 to about 1.3 µg/mg and having an $LD_{50}$ in mice of about 860 to about 1300 mg/kg.

2. The preparation of claim 1 wherein the $LD_{50}$ in mice is about 1250 mg/kg.

3. The preparation of claim 1 further having a therapeutic activity:toxic index ratio greater than about $2.6 \times 10^{-3}$.

4. The preparation of claim 1 further having a therapeutic activity:toxic index ratio from about $2.6 \times 10^{-3}$ to about $4.5 \times 10^{-3}$.

5. The preparation of claim 1 further having a therapeutic activity:toxic index ratio of about $4.5 \times 10^{-3}$.

6. A *Tripterygium wilfordii* Hook F preparation, obtainable by an alcohol extraction of the woody portion of the *Tripterygium wilfordii* Hook F root, having a triptolide concentration of about 0.2 to about 1.3 µg/mg.

7. The preparation of claim 6 having about 0.2 µg/mg triptolide.

8. A *Tripterygium wilfordii* Hook F preparation, obtainable by an ethanol extraction of the woody portion of the *Tripterygium wilfordii* Hook F root, having a triptolide concentration of about 0.2 to about 1.3 µg/mg and having an $ID_{50}$ in vitro T-cell proliferation/$LD_{50}$ ratio of between about $2.6 \times 10^{-3}$ to about $4.5 \times 10^{-3}$.

9. The preparation of claim 1 or 8 obtained by an ethyl acetate extraction of the root.

10. The preparation of claim 1, 6 or 8 obtained by an ethanol extraction followed by an ethyl acetate extraction.

11. A *Tripterygium wilfordii* Hook F preparation having about 0.2 to about 1.3 µg/mg triptolide obtained by a process comprising the steps of:

obtaining woody portions of roots of a *Tripterygium wilfordii* Hook F plant; and extracting the woody portions with a solvent to produce a *Tripterygium wilfordii* Hook F preparation;

wherein the preparation has about 0.2 to about 1.3 µg/mg triptolide.

12. The preparation of claim 11 wherein the solvent is ethyl acetate.

13. The preparation of claim 11 wherein the extracting step is comprised of two extractions with the first extraction utilizing an organic solvent and the second extraction utilizing a different organic solvent.

14. The preparation of claim 13 wherein the first solvent is ethanol and the second solvent is ethyl acetate.

15. A *Tripterygium wilfordii* Hook F preparation having a therapeutic activity:toxic index ratio of between about $2.6 \times 10^{-3}$ and about $5 \times 10^{-3}$ and having a triptolide concentration of about 0.2 to about 1.3 µg/mg, the preparation obtained by a process comprising the steps of:

obtaining woody portions of roots of a *Tripterygium wilfordii* Hook F plant;

extracting the woody portions with ethanol to produce an ethanol extract; and extracting the ethanol extract with ethyl acetate to form a *Tripterygium wilfordii* Hook F preparation;

wherein the preparation has a therapeutic activity:toxic index ratio of between about $2.6 \times 10^{-3}$ and about $5 \times 10^{-3}$.

16. The preparation of claim 15 further having an $LD_{50}$ in mice of greater than about 860 mg/kg to about 1300 mg/kg.

17. A *Tripterygium wilfordii* Hook F preparation having a therapeutic activity:toxic index ratio of about $4.5 \times 10^{-3}$ and having a triptolide concentration of about 0.2 µg/mg, the preparation obtained by a process comprising the steps of:

obtaining woody portions of roots of a *Tripterygium wilfordii* Hook F plant;

drying the woody portions to form a dried woody portion;

extracting the dried woody portion with alcohol to produce an alcohol extract; and extracting the alcohol extract with ethyl acetate to form a *Tripterygium wilfordii* Hook F preparation;

wherein the preparation has a therapeutic activity:toxic index ratio about $4.5 \times 10^{-3}$ and a triptolide concentration of about 0.2 µg/mg.

* * * * *